US010742687B2

(12) United States Patent
Pandian et al.

(10) Patent No.: US 10,742,687 B2
(45) Date of Patent: Aug. 11, 2020

(54) DETERMINING A DEVICE PROFILE AND ANOMALOUS BEHAVIOR ASSOCIATED WITH A DEVICE IN A NETWORK

(71) Applicant: Ordr Inc., Santa Clara, CA (US)

(72) Inventors: Gnanaprakasam Pandian, Cupertino, CA (US); Vivekanandan Vinayagam, San Ramon, CA (US); Sheausong Yang, Saratoga, CA (US); Vijayaraghavan Doraiswami, Santa Clara, CA (US); Krishna Kumar Vavilala, Bangalore (IN)

(73) Assignee: Ordr Inc., Santa Clara, CA (US)

( * ) Notice: Subject to any disclaimer, the term of this patent is extended or adjusted under 35 U.S.C. 154(b) by 190 days.

(21) Appl. No.: 16/117,897

(22) Filed: Aug. 30, 2018

(65) Prior Publication Data
US 2020/0076853 A1   Mar. 5, 2020

(51) Int. Cl.
*H04L 29/06*      (2006.01)
*H04L 29/12*      (2006.01)
*G16H 30/20*      (2018.01)
*G06N 20/00*      (2019.01)

(52) U.S. Cl.
CPC ............. *H04L 63/20* (2013.01); *G06N 20/00* (2019.01); *G16H 30/20* (2018.01); *H04L 61/1511* (2013.01); *H04L 61/2015* (2013.01); *H04L 63/102* (2013.01)

(58) Field of Classification Search
CPC . H04L 63/20; H04L 61/1511; H04L 61/2015; H04L 63/102; G06N 20/00; G16H 30/20
See application file for complete search history.

(56) References Cited

U.S. PATENT DOCUMENTS

| 5,926,180 | A | 7/1999 | Shimamura |
| 6,850,486 | B2 | 2/2005 | Saleh et al. |
| 8,185,824 | B1 | 5/2012 | Mitchell et al. |
| 8,332,782 | B1 | 12/2012 | Chang et al. |
| 8,631,459 | B2 * | 1/2014 | Choi ...................... G06F 21/57 709/217 |
| 2002/0042750 | A1 | 4/2002 | Morrison |
| 2006/0052998 | A1 | 3/2006 | Michelman |
| 2014/0157422 | A1 * | 6/2014 | Livshits .............. G06F 21/6245 726/26 |
| 2015/0163121 | A1 * | 6/2015 | Mahaffey ............ H04L 63/1425 707/687 |
| 2016/0337204 | A1 | 11/2016 | Dubey et al. |

(Continued)

*Primary Examiner* — Cheng-Feng Huang
(74) *Attorney, Agent, or Firm* — Invoke

(57) ABSTRACT

Techniques for determining a device profile and anomalous behavior associated with a device in a network are disclosed. Attribute values associated with a target device are determined based on data packets detected from a network. A subset of a set of classifiers associated with the available attribute values are selected. The attribute values are applied to the selected classifiers to determine a respective candidate device profile. A current device profile is determined for the target device based on the candidate device profiles. The current device profile indicates expected attribute values for the target device. Current attribute values are compared to the expected attribute values to determine whether there is any anomalous behavior associated with the target device.

23 Claims, 15 Drawing Sheets

(56) References Cited

U.S. PATENT DOCUMENTS

| | | | |
|---|---|---|---|
| 2017/0163502 A1* | 6/2017 | MacNeil | H04L 43/045 |
| 2018/0034655 A1 | 2/2018 | Christopher et al. | |
| 2018/0121032 A1 | 5/2018 | Naous et al. | |
| 2018/0121907 A1 | 5/2018 | Chisholm et al. | |
| 2018/0182137 A1 | 6/2018 | Pushpoth et al. | |
| 2018/0225592 A1* | 8/2018 | Ponnuswamy | G06F 16/35 |
| 2018/0234310 A1 | 8/2018 | Ingalls et al. | |
| 2019/0028289 A1* | 1/2019 | Saxena | G06F 21/56 |
| 2019/0319926 A1 | 10/2019 | Cummins et al. | |
| 2020/0007411 A1* | 1/2020 | Arar | H04L 41/22 |

* cited by examiner

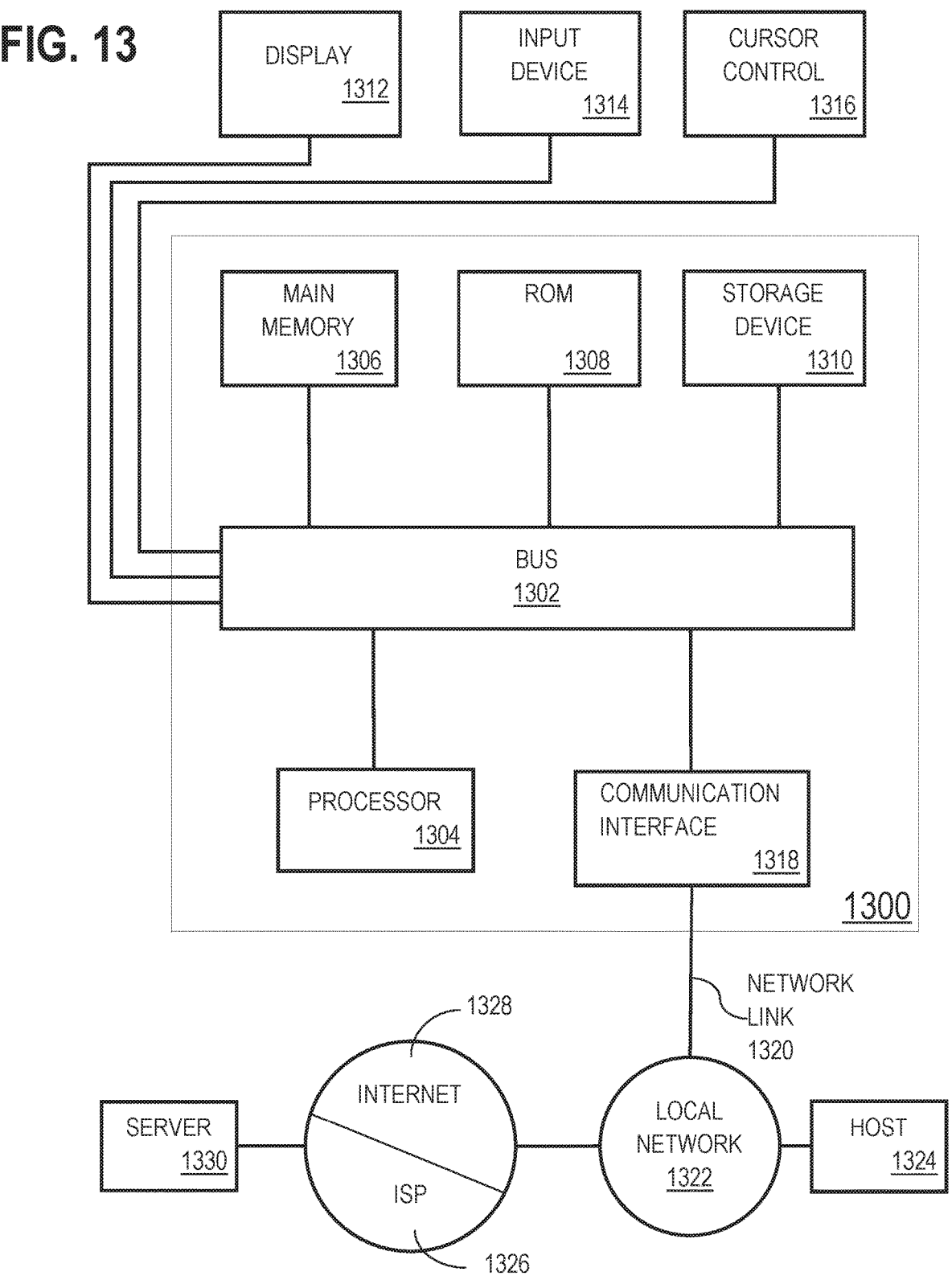

DETERMINING A DEVICE PROFILE AND ANOMALOUS BEHAVIOR ASSOCIATED WITH A DEVICE IN A NETWORK

RELATED APPLICATIONS; INCORPORATION BY REFERENCE

This application is related to U.S. Non-Provisional patent application Ser. No. 16/118,334, filed Aug. 30, 2018, which is hereby incorporated by reference.

The Applicant hereby rescinds any disclaimer of claim scope in any related application(s) or the prosecution history thereof and advises the USPTO that the claims in this application may be broader than any claim in the related application(s).

TECHNICAL FIELD

The present disclosure relates to devices in a network. In particular, the present disclosure relates to determining a device profile and anomalous behavior associated with a device in a network.

BACKGROUND

The term "Internet of Things" (IoT) refers to a network of a wide variety of devices, such as computers, sensors, vehicles, home appliances, medical equipment, and/or surveillance equipment. Such devices may be referred to as "IoT devices." Many IoT devices may connect to a network without explicit permission or acknowledgement from a network administrator. Many IoT devices may be easily relocated from one physical location to another physical location without explicit permission or acknowledgement from a network administrator. Many IoT devices may be easily relocated from one network location to another network location (for example, from one subnet to another subnet) without explicit permission or acknowledgement from a network administrator. Therefore, management of IoT devices (or any network with a large number devices) may be very difficult.

Moreover, an IoT device may be the subject of a network attack. As an example, a user may bring in a particular IoT device to a network. A network administrator might have no knowledge or control over the particular IoT device. The user does not perform regular software updates on the particular IoT device. Hence, the particular IoT device may have vulnerabilities to certain network attacks. The particular IoT device may become a weak entry point for an attacker. As another example, malicious software may be installed on a particular IoT device. Through a network connecting the particular IoT device with other devices, the particular IoT device may cause the malicious software to be installed on the other devices as well. Hence, a large number of devices in the network may become infected. Therefore, maintaining security in a network of IoT devices (or any network with a large number of devices) may be very difficult.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The embodiments are illustrated by way of example and not by way of limitation in the figures of the accompanying drawings. It should be noted that references to "an" or "one" embodiment in this disclosure are not necessarily to the same embodiment, and they mean at least one. In the drawings:

FIG. 13 shows a block diagram that illustrates a computer system in accordance with one or more embodiments.

DETAILED DESCRIPTION

Figure 1A:
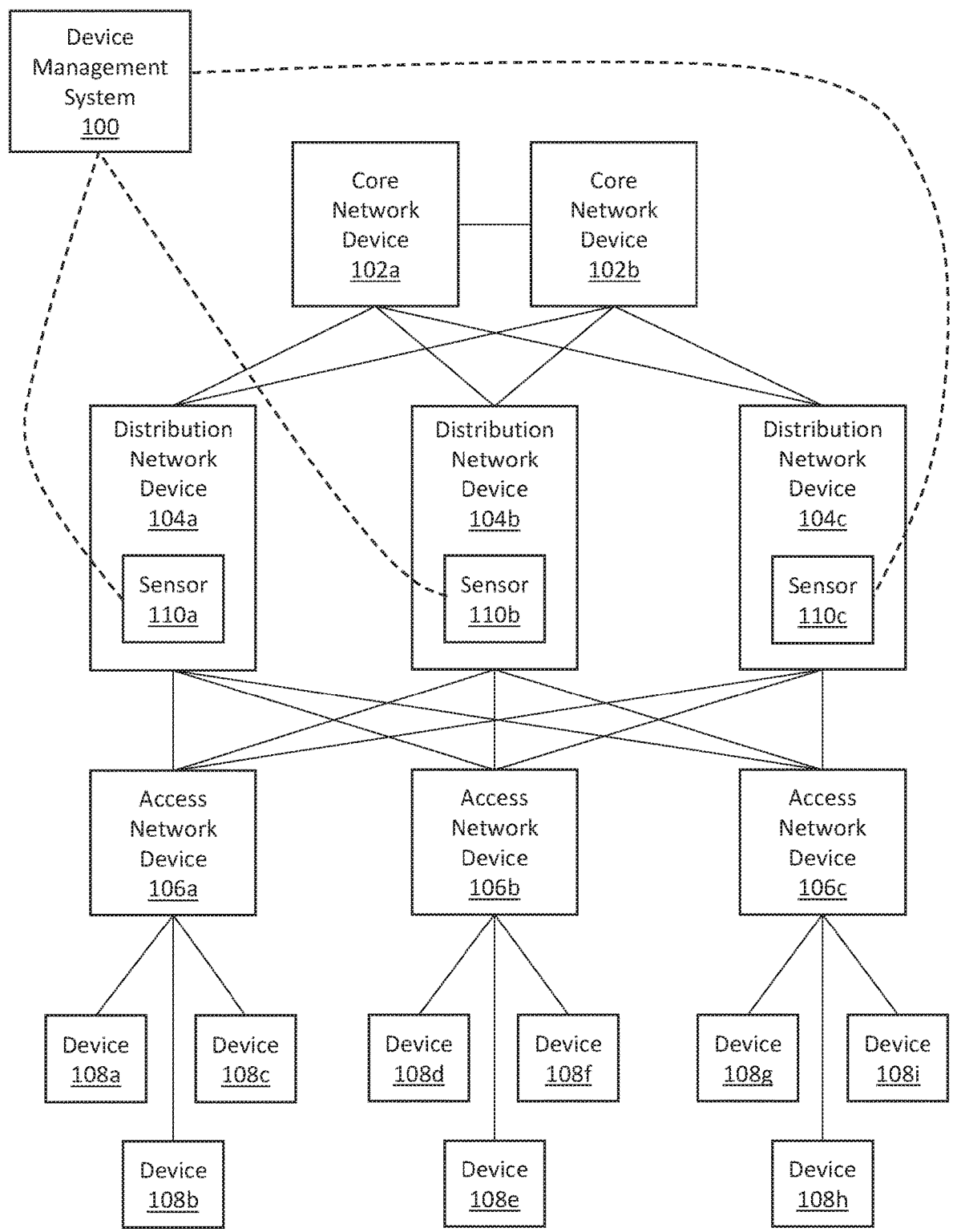
FIGS. 1A-B illustrate example networks including traffic sensors, in accordance with one or more embodiments.

In the following description, for the purposes of explanation, numerous specific details are set forth in order to provide a thorough understanding. One or more embodiments may be practiced without these specific details. Features described in one embodiment may be combined with features described in a different embodiment. In some examples, well-known structures and devices are described with reference to a block diagram form in order to avoid unnecessarily obscuring the present invention.

1. GENERAL OVERVIEW
2. TRAFFIC SENSORS IN A NETWORK
3. DEVICE MANAGEMENT SYSTEM ARCHITECTURE
4. EXAMPLE GRAPHICAL USER INTERFACES (GUI)
5. DETERMINING ATTRIBUTE VALUES ASSOCIATED WITH A DEVICE
6. DETERMINING A CURRENT DEVICE PROFILE FOR A DEVICE

7. PRESENTING, AT A GUI, DEVICE PHOTOS AND ASSOCIATED INFORMATION FOR DEVICES DETECTED IN A NETWORK
8. DETERMINING A RISK CATEGORY AND/OR ANOMALOUS BEHAVIOR OF A DEVICE
9. PRESENTING, AT A GUI, RISK CATEGORIES AND ASSOCIATED INFORMATION FOR DEVICES DETECTED IN A NETWORK
10. HARDWARE OVERVIEW
11. MISCELLANEOUS; EXTENSIONS

1. GENERAL OVERVIEW

One or more embodiments include detecting a set of devices communicating in a network. One or more sensors detect data packets communicated in a network. Each data packet is analyzed to determine one or more of: a device that transmitted the data packet, and a device that received the data packet. The set of devices communicating in the network include any device identified as transmitting and/or receiving a detected data packet. A set of devices that transmit and/or receive one or more data packets detected in the network may also be referred to herein as a "set of devices detected in a network."

One or more embodiments include determining values for attributes of a particular communication session conducted by a particular device in a network. One or more sensors detect data packets communicated in a network, including a particular set of data packets associated with a particular communication session conducted by a particular device. The particular set of data packets are analyzed to determine values for attributes of the particular communication session. A value for an attribute may also be referred to herein as an "attribute value."

Types of attributes include but are not limited to:
(a) Flow attributes: attributes associated with a flow of a communication session, including attributes associated with an Internet Protocol (such as, Internet Protocol version 4 (IPv4), Internet Protocol version 6 (IPv6)) used by a communication session;
(b) DNS attributes: attributes associated with a Domain Name System (DNS) protocol used by a communication session;
(c) DHCP attributes: attributes associated with a Dynamic Host Configuration Protocol DHCP) used by a communication session;
(d) DICOM attributes: attributes associated with a Digital Imaging and Communications in Medicine (DICOM) protocol used by a communication session;
(e) POCT attributes: attributes associated with a Point of Care Testing (POCT) protocol used by a communication session;
(f) CIP attributes: attributes associated with a Common Industrial Protocol (CIP) used by a
communication session;
(g) SIP attributes: attributes associated with a Session Initiation Protocol (SIP) used by a communication session;
(h) RTSP attributes: attributes associated with a Real Time Streaming Protocol (RTSP) used by a communication session; and/or
(i) BACnet attributes: attributes associated with a Building Automation and Control network (BACnet) protocol used by a communication session.

A value for a particular attribute of a communication session may or may not be ascertainable based on data packets that are currently detected. However, a value for the particular attribute may become ascertainable based on data packets that are subsequently detected. An attribute value that is currently ascertainable and determined is referred to herein as being "available." Conversely, an attribute value that is currently not ascertainable, or not determined, is referred to herein as being "unavailable."

One or more embodiments include determining a current device profile for a device detected in a network. A set of classifiers are used to determine a current device profile for a device. Each classifier takes as input one or more attribute values associated with the device. Attribute values associated with the device include attribute values of one or more communication sessions conducted by the particular device. However, as described above, not every attribute value may be available. Hence, only the classifiers that take as input the available attribute values, without taking as input any of the unavailable attribute values, are selected. Classifiers that take as input any of the unavailable attribute values are not selected. The available attribute values are applied respectively to the selected classifiers. Each classifier then outputs a candidate device profile for the device. Based on the candidate device profiles output from the selected classifiers, a current device profile is determined for the device. Based on the above approach, a system may determine current device profiles for the devices detected in a network, in order to manage and/or analyze the devices. Based on the above approach, the system need not wait for all attribute values to become available in order to determine a current device profile for a device. Rather, the system is able to take advantage of whatever attribute values are currently available to make a best determination on the current device profile for the device. Moreover, as more attribute values subsequently become available, the system may make another determination on the current device profile based on the increased amount of available information.

One or more embodiments include presenting, at a graphical user interface (GUI), device photos and associated information for devices detected in a network. Based on the available attribute values associated with each device, a device photo associated with each device is determined. A GUI concurrently presents device photos for the devices detected in a network. The device photos may be filtered, sorted, grouped, and/or visualized based on an analysis criteria. As an example, there may be different visualizations for (a) device photos corresponding to device types that are expected in a network and (b) device photos corresponding to device types that are not expected in a network. As another example, all devices of a same device category may be grouped together and represented by a single device photo corresponding to the device category. As another example, device photos may be sorted by a level of risk associated with the corresponding devices. Based on the above approach, a GUI may present information about the devices detected in a network in a easily understandable manner to a user. Due to the proliferation of IoT devices, and the ease at which an IoT device may connect to a network, there may be a very large number of devices in a network. The devices detected in a network may be presented in textual form, such as a list of names corresponding to the devices. However, a textual listing of device names may be difficult for a user to review. In contrast, a user is able to quickly scan a large number of device photos to determine whether extraneous devices exist in the network. Moreover, a user who manages the network is not necessarily familiar with the devices that should be in the network. As an example, the user may be an Information Technology (IT) Administrator, while the devices in the network may be medical devices used by medical professionals. Hence, merely a textual listing of device names might not be helpful for the IT Administrator in understanding what devices are in the network. In contrast, a device photo helps the IT Administrator quickly visualize what devices are in the network. The IT Administrator may also be able to quickly locate a particular device in physical environment based on a device photo of the particular device shown at a GUI. Conversely, the IT Administrator may be able to quickly locate a device photo of a particular device, as shown at a GUI, based on seeing the particular device in a physical environment. The IT Administrator may then be able to select an icon associated with the device photo shown at the GUI to request additional information about the particular device.

One or more embodiments include determining anomalous behavior performed by a device detected in a network. Based on the available attribute values associated with a device, expected attribute values for the device are determined. If attribute values that are currently detected are outside of the expected attribute values, then the device is determined as exhibiting anomalous behavior. One or more corrective actions may be performed. As an example, a corrective action may be presenting and/or transmitting an alert. As another example, a corrective action may be blocking, redirecting, and/or controlling communications to and/or from the device. If attribute values that are currently detected are within the expected attribute values, then the device is not determined as exhibiting anomalous behavior. Based on the above approach, anomalous behavior may be accurately determined. Moreover, the classifiers and/or expected attribute values may be learned and updated via machine learning. As such, changes in the normal use of the devices may be reflected in the system without manual input. Hence, even a network of a large number of IoT devices and/or other devices, anomalous behavior may be accurately determined and properly addressed.

One or more embodiments include presenting, at a GUI, risk categories and associated information for devices detected in a network. A risk category for a device may be referred to herein as a "device risk category." A device risk category may be determined based on a variety of factors, such as a risk score determined for a device, anomalous behavior of the device, network address(es) with which the device is communicating, and/or a device type of the device. A risk category for a particular incident may be referred to herein as an "incident risk category." An incident risk category may be determined based on a variety of factors, such as source and/or destination network addresses of a communication session, amount of data communicated in the communication session, type of application conducting the communication session, and/or operations performed using the communication session. A GUI concurrently presents icons representing sets of risk categories. The GUI also presents information associated with each risk category, such as the number of devices in each risk category, and/or the number of incidents in each risk category. Based on the above approach, a GUI may present risk information associated with devices and communication sessions in a network. Rather than reading through lines of text to obtain an assessment of a network, a user may view the GUI to gain an overall picture of the level of risk that the network is exposed to. A user may also drill down on a particular risk category to further understand the devices and/or incidents involved and thereby address the issue.

One or more embodiments described in this Specification and/or recited in the claims may not be included in this General Overview section.

2. TRAFFIC SENSORS IN A NETWORK

Figure 1B:
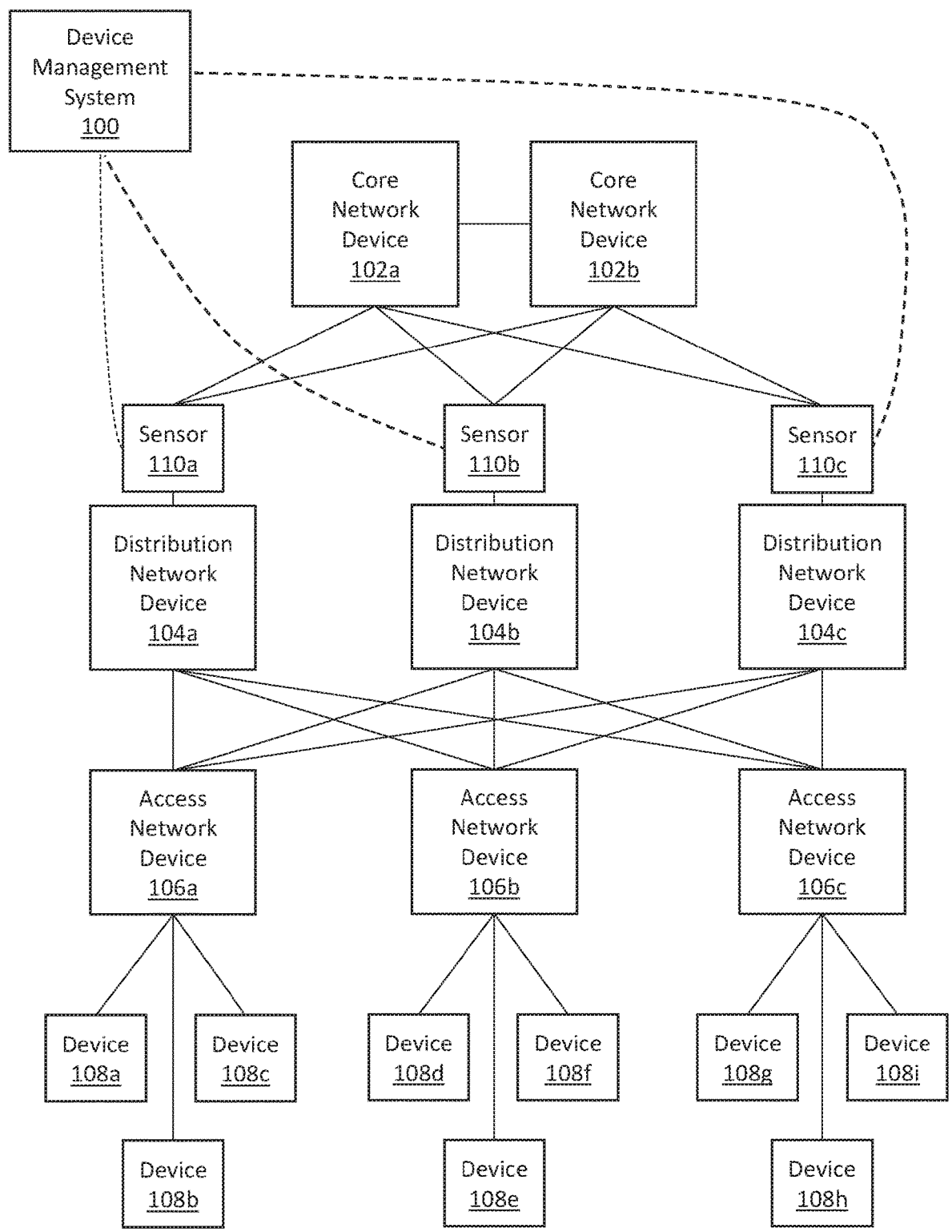

FIGS. 1A-B illustrate example networks including traffic sensors, in accordance with one or more embodiments.

In one or more embodiments, a network device is configured to connect end devices in a network. Examples of network devices include routers, switches, bridges, hubs, and/or gateways. An end device is a source device or a destination device in a network. Examples of end devices include computers, printers, servers, smartphones, smart appliances, security cameras, networked medical equipment, networked manufacturing machines, networked sensors, and/or IoT devices.

In one or more embodiments, a set of network devices implementing a network are arranged in a network hierarchy. The network hierarchy includes one or more of the following layers: a core layer, a distribution layer, and an access layer.

A core layer is considered a backbone of the network. The core layer includes a set of core network devices 102a-b that are typically associated with the highest speed and/or efficiency, as compared to network devices in the other layers of the network hierarchy. The core network devices 102a-b may be used to merge geographically-separated networks. [37] A distribution layer is positioned between a core layer and an access layer. The distribution layer provides policy-based connectivity between the access and core layers. The distribution layer thereby controls the boundary between the access and core layers. The distribution layer may achieve boundary control by implementing access lists and other filters. The distribution layer includes a set of distribution network devices 104a-c that route traffic between subnets, virtual local area networks (VLANs), and/or broadcast domains in the network.

An access layer provides workgroups and/or users access to the network. The access layer includes a set of access network devices 106a-c connected to end devices 108a-h. The access layer may include access points (APs) to wirelessly connect end devices to the network. As illustrated, access network device 106a connects end devices 108a-c to the network. Access network device 106b connects end devices 108d-f to the network. Access network device 106c connects end devices 108g-i to the network.

In one or more embodiments, a traffic sensor (such as, sensors 110a-c) is configured to capture data packets transmitted to and/or from a device in a network. A traffic sensor may be configured as a Test Access Point (TAP) or a Switched Port Analyzer (SPAN). A traffic sensor may also be used in alternate configurations.

In one or more embodiments, sensors 110a-c are attached to the distribution layer of a network hierarchy. Since the distribution layer processes traffic between subnets, virtual local area networks (VLANs), and/or broadcast domains of the network, sensors 110a-c attached to the distribution layer may be able to capture a significant portion of all traffic in the network.

Referring to the example illustrated in FIG. 1A, sensors 110a-c are implemented respectively within distribution network devices 104a-c. As a distribution network device routes traffic from one port to another port, a sensor of the distribution network device sends a copy of the traffic to a SPAN port (also known as a mirror port). Data packets are hence captured at the SPAN port of the distribution network device for analysis. Data packets are transmitted from the SPAN port to a device management system 100. A device management system 100 is further described below with reference to FIG. 2.

Referring to the example illustrated in FIG. 1B, sensors 110a-c are positioned in-line between the distribution layer and the core layer. As illustrated, sensor 110a is between distribution network device 104a and core network device 102a. Sensor 110b is between distribution network device 104b and core network device 102b. Sensor 110c is between distribution network device 104c and core network device 102c. A sensor performs a passive splitting mechanism. The sensor receives traffic through a particular port. The sensor then forwards the traffic to at least two ports: one port associated with the intended destination of the traffic, and a monitoring port. Data packets are hence captured at the monitoring port of the sensor for analysis. Data packets are transmitted from the monitoring port to a device management system 100. A device management system 100 is further described below with reference to FIG. 2.

In other embodiments, sensors 110a-c are attached to additional or alternative layers of the network hierarchy. For example, sensors may be attached to one or more core network devices 102a-b, and/or one or more access network devices 106a-c. In yet other embodiments, network devices may be arranged differently, and sensors 110a-c may be attached to the network devices in a different arrangement.

3. DEVICE MANAGEMENT SYSTEM ARCHITECTURE

Figure 2:
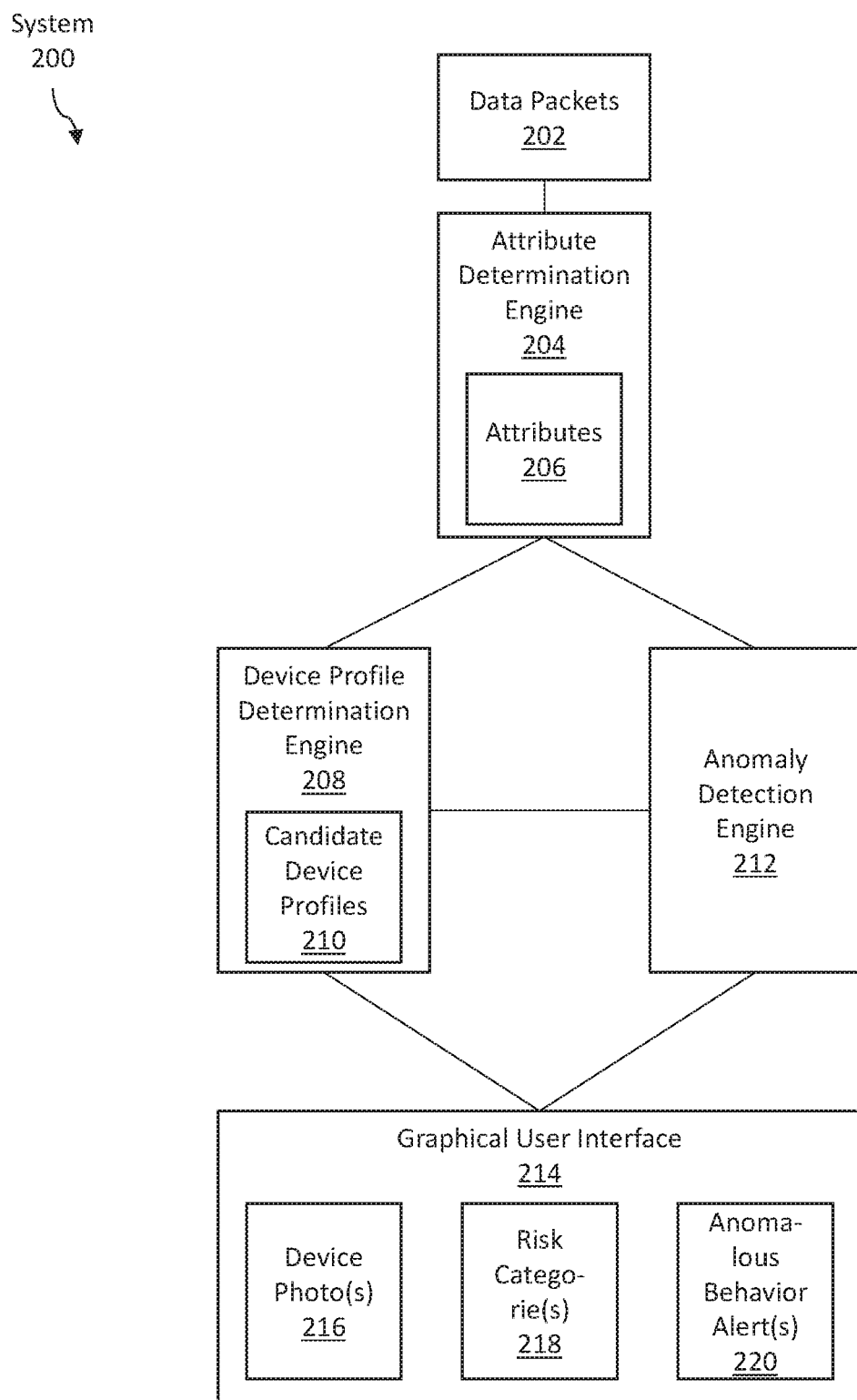
FIG. 2 illustrates an example device management system, in accordance with one or more embodiments.

FIG. 2 illustrates an example device management system, in accordance with one or more embodiments. As illustrated in FIG. 2, a system 200 includes data packets 202 captured from a network, an attribute determination engine 204, a device profile determination engine 208, an anomaly detection engine 212, and a graphical user interface (GUI) 214. In one or more embodiments, the system 200 may include more or fewer components than the components illustrated in FIG. 2. The components illustrated in FIG. 2 may be local to or remote from each other. The components illustrated in FIG. 2 may be implemented in software and/or hardware. Each component may be distributed over multiple applications and/or machines. Multiple components may be combined into one application and/or machine. Operations described with respect to one component may instead be performed by another component.

In one or more embodiments, data packets 202 are data packets that are captured from a network (such as the networks shown in FIGS. 1A-B). The data packets 202 are communicated to and/or from one or more devices in the network. The data packets 202 may be communicated internally within the network. Additionally or alternatively, the data packets 202 may be communicated externally to an external network (such as, the Internet). As described above, a sensor may capture data packets 202 at a distribution layer of a network hierarchy, and/or at other layers of the network hierarchy. A sensor may be configured as a TAP or SPAN to capture data packets 202. Different arrangements of sensors on different network structures may also be used.

In one or more embodiments, an attribute determination engine 204 refers to software and/or hardware configured to determine values for a set of attributes 206 of communication sessions conducted by devices in a network. A value for an attribute may also be referred to herein as an "attribute value." Examples of operations for determining attribute values for a communication session conducted by a device in a network are described below with reference to FIG. 8.

In one or more embodiments, types of attributes include but are not limited to:

(a) Flow attributes: attributes associated with a flow of a communication session, including attributes associated with an Internet Protocol (such as, Internet Protocol version 4 (IPv4), Internet Protocol version 6 (IPv6)) used by a communication session;
(b) DNS attributes: attributes associated with a Domain Name System (DNS) protocol used by a communication session;
(c) DHCP attributes: attributes associated with a Dynamic Host Configuration Protocol (DHCP) used by a communication session;
(d) DICOM attributes: attributes associated with a Digital Imaging and Communications in Medicine (DICOM) protocol used by a communication session;
(e) POCT attributes: attributes associated with a Point of Care Testing (POCT) protocol used by a communication session;
(f) CIP attributes: attributes associated with a Common Industrial Protocol (CIP) used by a communication session;
(g) SIP attributes: attributes associated with a Session Initiation Protocol (SIP) used by a communication session;
(h) RTSP attributes: attributes associated with a Real Time Streaming Protocol (RTSP) used by a communication session; and/or
(i) BACnet attributes: attributes associated with a Building Automation and Control network (BACnet) protocol used by a communication session.

Attributes associated with a flow of a communication session may include any of: a source address (such as an IP address and/or a Media Access Control (MAC) address); a destination address; a source port; a destination port; a number of transmitted bytes; a number of received bytes; a source subnet; and a destination subnet.

Attributes associated with a particular protocol (such as, IPv4, IPv6, DNS, DICOM, POCT, CIP, SIP, RTSP, DHCP, and BACnet) include values for standard fields specified and/or defined by a corresponding protocol specification. The standard fields may be included in a header, tail, and/or other portion of a data packet.

As an example, standard fields in an IPv4 data packet include any of: Internet Protocol Version; Internet Header Length; Differentiated Services Code Point (DSCP); Explicit Congestion Notification (ECN); Total Length; Identification (for example, for identifying the group of fragments of a single IP datagram); Flags; Fragment Offset; Time to Live (TTL); Protocol (for example, for defining the protocol used in the data portion of the IP datagram); Header Checksum; Source Address; Destination Address; and Options. Additional and/or alternative standard fields may be used. A value for a standard field in an IPv4 data packet may be a value for an attribute 206 of a communication session.

As another example, standard fields in a DNS query or response include any of: Identification; Flags; Number of Questions; Number of Answers; Number of Authority Resource Records (RRs); Number of Additional RRs; Request Type. Additional and/or alternative standard fields may be used. A value for a standard field in a DNS query or response may be a value for an attribute 206 of a communication session.

As another example, standard fields in a DHCP packet include any of: MAC address; IP address; subnet; host name; DHCP Options; DHCP Class Identifier; Manufacturer; DHCP Parameter List; and DHCP Vendor Class. Additional and/or alternative standard fields may be used. A value for a standard field in a DHCP data packet may be a value for an attribute 206 of a communication session.

As another example, DICOM is a protocol for the communication and management of medical imaging information and related data. Standard fields in a DICOM data packet include any of: Creation Time; Manufacturer; Institution Name; Referring Physician's Name; Consulting Physician's Name; Operator's Name; Warning Reason; Failure Reason; Patient's Name; Patient Identifier; Patient's Birth Date; Patient's Sex; Image Size. Additional and/or alternative standard fields may be used. A value for a standard field in a DICOM data packet may be a value for an attribute 206 of a communication session.

Additionally or alternatively, an attribute 206 of a communication session may include statistics and/or characteristics of the communication session. For example, attributes may include any of: a number of data packets in the communication session; a number of communication sessions that share a common set of attribute values; a frequency of communication sessions that share a common set of attribute values; a duration of the communication session; and whether or not the communication session is secure.

In one or more embodiments, a device profile determine engine 208 refers to software and/or hardware configured to determine a current device profile, from a set of candidate device profiles 210, for a device detected in a network. Examples of operations for determining a current device profile for a device detected in a network are described below with reference to FIG. 9.

Figure 3:
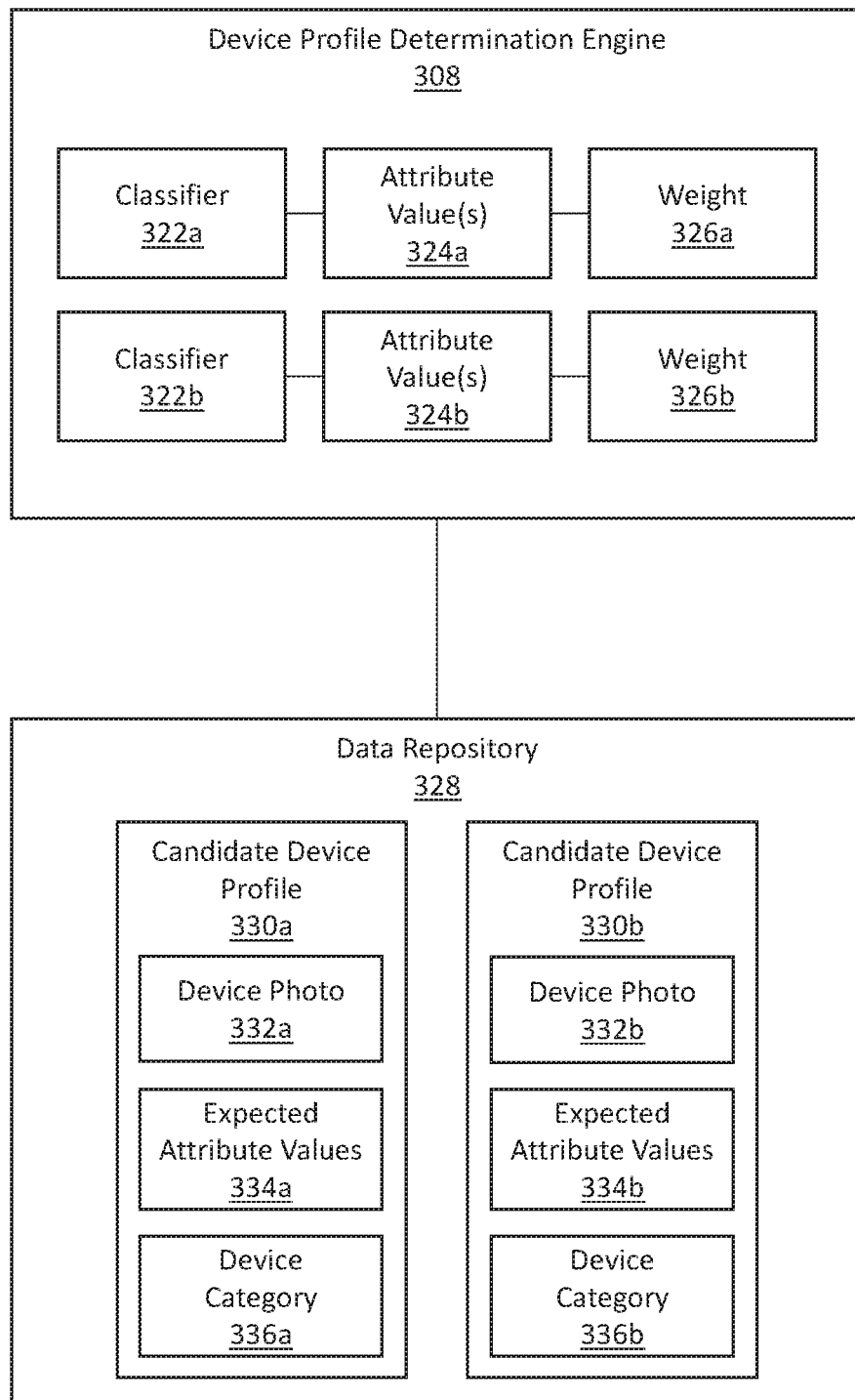
FIG. 3 illustrates an example device profile determination engine, in accordance with one or more embodiments.

Referring to FIG. 3, FIG. 3 illustrates an example device profile determination engine, in accordance with one or more embodiments. A device profile determination engine 308 of FIG. 3 is similar to the device profile determination engine 208 of FIG. 2. Candidate device profiles 330a-b of FIG. 3 are similar to the candidate device profiles 210 of FIG. 2.

In one or more embodiments, a device profile determination engine 308 may utilize one or more classifiers 322a-b for determining a current device profile for a device. Each classifier takes as input one or more attribute values associated with a particular device. As illustrated, classifier 322a takes as input one or more attribute values 324a; classifier 322b takes as input one or more attribute values 324b. Different attribute values are input to different classifiers; however, attribute values input to different classifiers may overlap with each other. Based on the inputted attribute values, each classifier outputs a respective candidate device profile, from a set of candidate device profiles 330a-b, for a device. Further description regarding candidate device profiles 330a-b are included below.

In an embodiment, each classifier corresponds to an attribute type. Each classifier takes as input attribute values for attributes of the corresponding attribute type. A classifier does not take as input any attribute values associated with attribute types other than the corresponding attribute type. As an example, classifier 322a may correspond to flow attributes. Classifier 322a may take as input, for example, an Internet Header Length value, a DSCP value, a Total Length value, and a Flags value. Meanwhile, classifier 322b may correspond to DICOM attributes. Classifier 322b may take as input, for example, a Creation Time value, a Manufacturer value, a Consulting Physician's Name value, and an Image Size value.

In other embodiments, classifiers 322a-b are randomly associated with the attributes. A first classifier may take as input an attribute value associated with a first attribute type, and an attribute value associated with a second attribute type. A second classifier may take as input an attribute value associated with the second attribute type, and an attribute value associated with a third attribute type.

Classifiers 322a-b may be generated based on machine learning and/or other algorithms. In an embodiment, a classifier may be expressed in the form of a decision tree. Based on various input parameters, the decision tree is traversed. A final node of the decision tree outputs a candidate device profile for a device. In other embodiments, other forms of classifiers may be used.

In an embodiment, each classifier is associated with a weight. As illustrated, classifier 322a is associated with weight 326a; classifier 322b is associated with weight 326b. The weight associated with a particular classifier represents a significance of a candidate device profile output from the particular classifier for a device, as compared to candidate device profiles output from other classifiers. In particular, each candidate device profile output from a respective classifier, for a device, is weighted by the weight associated with the respective classifier. The candidate device profiles, together with the associated weights, are used to determine a current device profile for a device. Examples of operations for determining a current device profile based on candidate device profiles and associated weights is described below with reference to FIG. 9.

The weight associated with a particular classifier may depend on the attributes associated with the particular classifier. As an example, the use of DICOM attribute values may determine a device profile for a device more accurately than the use of flow attribute values. Hence, a classifier that takes as input DICOM attribute values may be associated with a greater weight than a classifier that takes as input flow attribute values.

In one or more embodiments, a candidate device profile (such as, any of candidate device profiles 330a-b) indicates (a) a device photo for a device, (b) expected attribute values associated with a device, and/or (c) a device category. As illustrated, candidate device profiles 330a is associated with device photo 332a, expected attribute values 334a, and device category 336a; candidate device profiles 330b is associated with device photo 332b, expected attribute values 334b, and device category 336b.

In an embodiment, a device photo associated with a candidate device profile may be obtained based on user input. Additionally or alternatively, a device photo associated with a candidate device profile may be obtained by a system. As an example, a system may crawl the web for device photos. A system may map a device photo to a particular device profile based on a context surrounding the device photo on the web. As another example, a security camera may capture a photo of a particular device located at a physical location. A current device profile (which does not currently include any device photo) may be determined for the particular device. A system may determine that the particular device is located at the physical location where the photo was captured by the security camera. Based on the matching physical locations, the system may map the captured photo to the current device profile determined for the particular device. As another example, a system may obtain a set of user manuals for various devices. The system may obtain device photos from the user manuals.

In an embodiment, the expected attribute values of a candidate device profile may be determined via supervised machine learning and/or unsupervised machine learning. An example machine learning algorithm is clustering. Attribute values detected over a particular time period may be input into the clustering algorithm. The clustering algorithm finds a certain number of cluster centers (also known as "centroids"). Each cluster center represents a different candidate device profile. The attribute values at a cluster center are expected values for the corresponding candidate device profile. Additionally, based on a distribution of the detected attribute values, a range of values surrounding a cluster center may also be included in the expected values for the corresponding candidate device profile.

A candidate device profile may indicate multiple expected values, or a range of expected values, for an attribute. As an example, a candidate device profile may indicate that the bytes communicated in a communication session are within the range 10 KB to 50 KB. As another example, a candidate device profile may indicate that the Consulting Physician's Name attribute in a DICOM data packet are one of: John Smith, Ada Wong, or Henry Seto.

A candidate device profile may indicate a single expected value for an attribute. As an example, a candidate device profile may indicate that the Consulting Physician's Name attribute in a DICOM data packet is Henry Seto.

A candidate device profile may indicate that an expected value for an attribute is null. The null value indicates that the attribute value should be unavailable. As an example, a candidate device profile may indicate that the value of any POCT attributes is null. Hence, any values for the POCT attributes should be unavailable.

As an example, a particular medical device profile may indicate the following:
(a) Flow attributes: bytes communicated in a communication session are within the range 10 KB to 50 KB; frequency of communication sessions is within once every 30 minutes to once every 60 minutes; and duration of communication sessions is within the range of 0.5 seconds to 1.5 seconds.
(b) DNS attributes: query type of a DNS query communicated during a communication session is limited to requests for IPv4 address records (that is, there should be no request IPv6 address records)
(d) DICOM attributes: size of image communicated during a communication session is within the range of 0 MB and 100 MB;
(e) POCT attributes: null (that is, the POCT attribute values should be unavailable); and
(f) Traffic statistics: setup time for a Transmission Control Protocol (TCP) session is under a threshold of 1 second; a number of retransmissions of a particular data packet is under a threshold of 5 times.

In an embodiment, a device category includes a set of candidate device profiles that share characteristics. As an example, a device category may be medical devices. Candidate device profiles within the medical devices category may include infusion pump, heart rate monitor, and x-ray machine. Another device category may be printers and copiers. Candidate device profiles within the printers and copiers category may include printer, copier, scanner, and facsimile machine. Another device category may be appliances. Candidate device profiles within the appliances category may include toaster, microwave, and refrigerator.

In one or more embodiments, a data repository 328 is any type of storage unit and/or device (e.g., a file system, database, collection of tables, or any other storage mechanism) for storing data. Further, a data repository 328 may include multiple different storage units and/or devices. The multiple different storage units and/or devices may or may not be of the same type or located at the same physical site. Further, a data repository 328 may be implemented or may execute on the same computing system as a device profile determination engine 308. Alternatively or additionally, a data repository 328 may be implemented or executed on a computing system separate from a device profile determination engine 308. The data repository 328 may be communicatively coupled to the device profile determination engine 308 via a direct connection or via a network.

Information describing candidate device profiles 330a-b may be implemented across any of components within a device management system. However, this information is illustrated within the data repository 328 for purposes of clarity and explanation.

Referring back to FIG. 2, in one or more embodiments, an anomaly detection engine 212 refers to hardware and/or software configured to determine a risk category and/or anomalous behavior of a device detected in a network. An anomaly detection engine 212 determines anomalous behavior of a device based on a current device profile for the device. The anomaly detection engine 212 determines that the device is exhibiting anomalous behavior if the detected attribute values associated with the device fall outside of the expected attribute values specified by the current device profile. In response to detecting anomalous behavior, corrective action may be performed. Examples of operations for determining a risk category and/or anomalous behavior of a device detected in a network are described below with reference to FIG. 11.

In one or more embodiments, a graphical user interface (GUI) 214 refers to hardware and/or software configured to facilitate communications between (a) a user and (b) an attribute determination engine 204, a device profile determination engine 208, and/or an anomaly detection engine 212. A GUI 214 may be rendered and/or displayed on a screen and/or monitor. A GUI 214 may present one or more interface elements for presenting information to a user and/or for receiving information from a user. Examples of interface elements include checkboxes, radio buttons, drop-down lists, list boxes, buttons, toggles, text fields, date and time selectors, command lines, sliders, pages, and/or forms. Other types of user interfaces include a command line interface (CLI), a haptic interface, and a voice command interface.

Components of a GUI 214 may be specified in one or more languages, such as Java, C, and/or C++. In some embodiments, the behavior of interface elements is specified in a dynamic programming language, such as JavaScript. The content of interface elements is specified in a markup language, such as hypertext markup language (HTML) or XML User Interface Language (XUL). The layout of interface elements is specified in a style sheet language, such as Cascading Style Sheets (CSS).

In an embodiment, a GUI 214 presents one or more device photos 216, one or more risk categories 218, and/or one or more anomalous behavior alerts 220. Device photos 216 of FIG. 2 are similar to device photos 332a-b of FIG. 3.

In an embodiment, multiple device photos 216 are concurrently presented at a GUI 214 to indicate a set of devices, associated respectively with the presented device photos 216, have been detected in a network. A device may be associated with a particular device photo 216 if (a) a particular candidate device profile has been determined as a current device profile for the device and (b) the particular candidate device profile is associated with the particular device photo 216. An icon associated with each device photo 216 is selectable to request additional information about a device associated with the selected device photo 216.

In an embodiment, multiple risk categories 218 are concurrently presented at a GUI 214 to indicate risks associated with a set of devices detected in a network. Each risk category indicates a level of risk associated with a device and/or an incident in the network. The GUI 214 may present a number of devices in each risk category 218. Additionally, an icon associated with each risk category 218 is selectable to request additional information about the selected risk category 218, such as devices and/or communication sessions within the selected risk category 218.

In an embodiment, an anomalous behavior alert 220 is presented at a GUI 214, other user interface, and/or application programming interface (API) to indicate that a device exhibits anomalous behavior. As described above, an anomalous behavior may be determined based on a current device profile for a device. Based on an anomalous behavior alert 220, a user and/or another application may perform further corrective action.

In one or more embodiments, an attribute determination engine 204, a device profile determination engine 208, an anomaly detection engine 212, and/or a GUI 214 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware firewall, a hardware network address translator (NAT), a hardware load balancer, an access point, a mainframe, a television, a content receiver, a set-top box, a printer, a mobile handset, a smartphone, a personal digital assistant (PDA), and/or a traffic sensor.

4. EXAMPLE GRAPHICAL USER INTERFACES (GUI)

Figure 4:
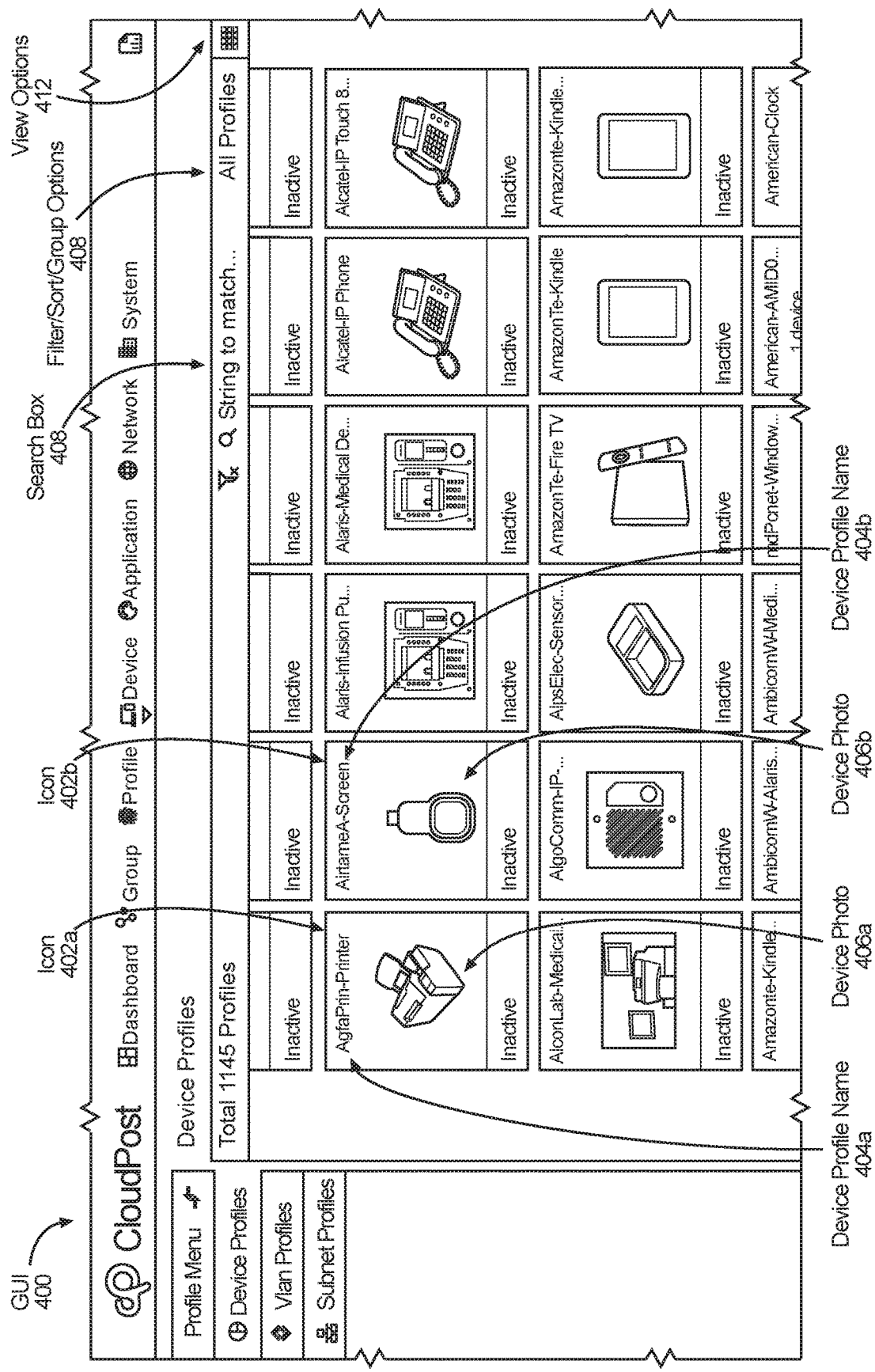
FIG. 4 illustrates an example graphical user interface (GUI) showing device photos of devices detected in a network, in accordance with one or more embodiments.

FIG. 4 illustrates an example graphical user interface (GUI) showing device photos of devices detected in a network, in accordance with one or more embodiments. As illustrated, GUI 400 shows a list of devices detected in a network. In particular, GUI 400 shows the devices in the network by concurrently showing device photos, such as device photos 406*a*-*b*, associated with the devices. Each device photo is associated with an icon and a device profile name. As an example, device photo 406*a* is associated with icon 402*a* and device profile name 404*a*; device photo 406*b* is associated with icon 402*b* and device profile name 404*b*. Each icon is selectable to request additional information about the associated device.

In an embodiment, each device profile is associated with a device photo. Hence, devices associated with a same device profile are presented using a same device photo. Multiple device profiles may also optionally share a same device photo.

Also as illustrated, GUI 400 shows a search box 408, filter/sort/group options 410, and view options 412. Search box 408 is configured to receive user input specifying a search query. As an example, a user may enter a particular device profile name into the search box 408. Responsive to the search query for the particular device profile name, GUI 400 may show device photos corresponding to each device that is associated with the particular device profile name.

Filter/sort/group options 410 are configured to receive user input specifying whether to filter, sort, and/or group the device photos. Additionally or alternatively, filter/sort/group options 410 are configured to receive user input specifying one or more analysis criteria for filtering, sorting, and/or grouping the device photos. As an example, a user may request grouping by device profile name. Hence, all devices corresponding to a same device profile name are grouped into a single group. A group of devices may be represented by a single device photo that is associated with the device profile common to the group of devices. The GUI 400 may present a set of device photos, each corresponding to a group of devices that share a common device profile. As another example, a user may request filtering based on a list of registered device profiles. Devices that are associated with any of the registered device profiles are filtered out and not presented at the GUI 400. The remaining devices are presented at the GUI 400. As another example, a user may request sorting based on risk scores associated with the devices. The GUI 400 may present device photos associated with high-risk devices before device photos associated with low-risk devices. Additional or alternative filtering, sorting, and/or grouping criteria may also be used.

View options 412 are configured to receive user input specifying a desired format to view a list of devices detected in a network. One view option is a photo view. GUI 400 as illustrated presents the photo view. GUI 400 indicates the devices detected in the network by presenting device photos. Another view option is textual view. GUI 400 may present the names of the devices detected in the network, without presenting the device photos. Additional or alternative view options may also be used.

Figure 5:
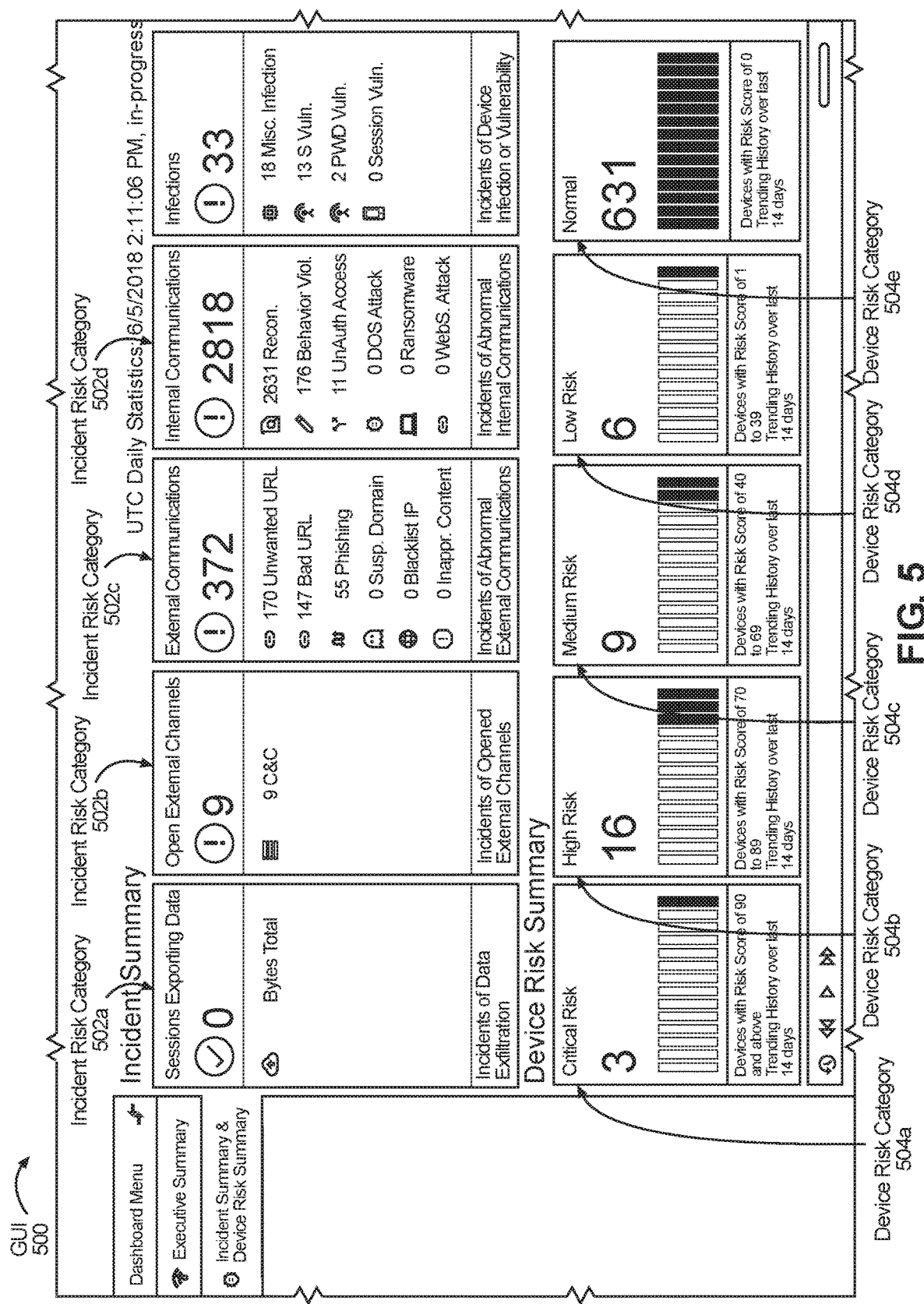
FIG. 5 illustrates an example GUI showing risk categories and associated information, in accordance with one or more embodiments.

FIG. 5 illustrates an example GUI showing risk categories and associated information, in accordance with one or more embodiments. As illustrated, GUI 500 shows two sets of risk categories.

Risk categories 502*a*-*d* are incident risk categories, which indicate a level of risk associated with each incident. Risk category 502*a*, named "Sessions Exporting Data," includes communication sessions that export data. Risk category 502*b*, named "Open External Channels," includes communication sessions that are associated with open external channels. For example, the communication sessions may involve communicating with a command and control (C&C) center. Risk category 502*c*, named "External Communications," includes communication sessions that communicate with network addresses external to the network. For example, the communication sessions may communicate with network addresses over the Internet. Risk category 502*d*, named "Internal Communications," includes communication sessions that communicate with network addresses internal to the network.

Risk categories 504*a*-*e* are device risk categories, which indicate a level of risk associated with each device. Each risk category 504*a*-*e* is associated with a respective range of risk scores. A device associated with a risk score within a particular range is categorized into the corresponding risk category. Risk category 504*a* includes devices associated with "critical risk," which includes devices associated with the highest risk scores. Risk category 504*b* includes devices associated with "high risk." Risk category 504*c* includes devices associated with "medium risk." Risk category 504*d* includes devices associated with "low risk." Risk category 504*e* includes devices that are considered "normal," which includes devices associated with the lowest risk scores.

The GUI 500 shows information associated with each risk category.

For risk categories 502*a*-*d*, the GUI 500 may show a breakdown according to communication types. For the "Open External Channels" category, the GUI presents a number of incidents corresponding to C&C centers. For the "External Communications" category, the GUI presents a number of incidents corresponding to each of: "Unwanted URL," "Bad URL," "Phishing," "Suspicious Domain," "Blacklist IP," and "Inappropriate Content." For the "Internal Communications" category, the GUI presents a number of incidents corresponding to each of: "Network Reconnaissance," "Behavior Violations," "Unauthorized Access," "Denial-of-Service Attack," "Ransomware," and "Web Attack."

For risk categories 504a-e, the GUI 500 may show bar graphs indicating a proportion of devices in the network that are categorized into each category. As illustrated, for example, the GUI 500 shows 3 devices in the "Critical Risk" category, using one unit in the bar to indicate a proportion of devices in the category. The GUI 500 shows 16 devices in the "High Risk" category, using three units in the bar to indicate a proportion of devices in the category. The GUI 500 shows 9 devices in the "Medium Risk" category, using two units in the bar to indicate a proportion of devices in the category. The GUI 500 shows 6 devices in the "Low Risk" category, using one unit in the bar to indicate a proportion of devices in the category. The GUI 500 shows 631 devices in the "Normal" category, using fourteen units in the bar to indicate a proportion of devices in the category.

Each risk category is selectable to request additional information about the risk category.

Figure 6:
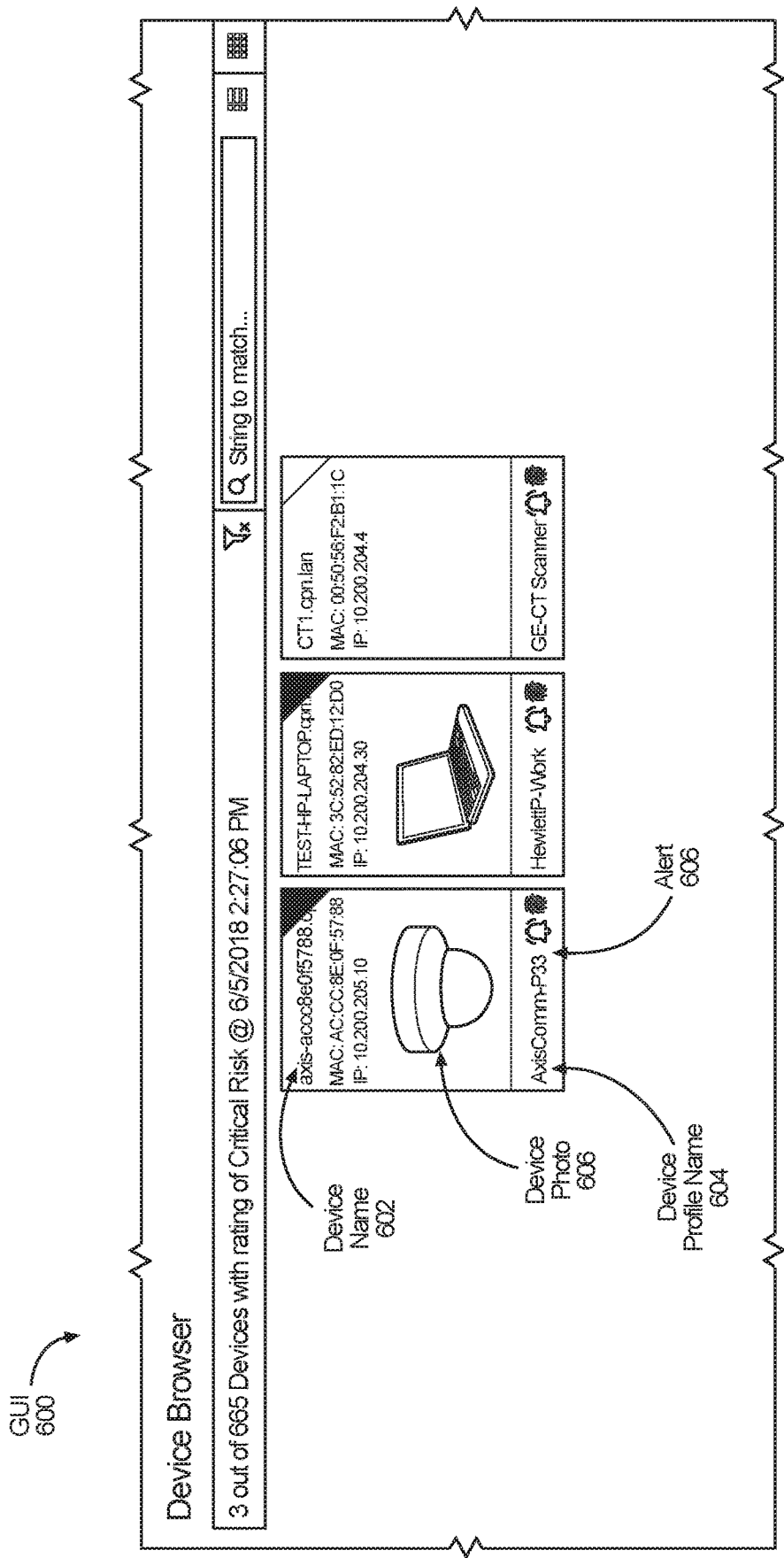
FIG. 6 illustrates an example GUI showing device photos of devices associated with a particular risk category, in accordance with one or more embodiments.

FIG. 6 illustrates an example GUI showing device photos of devices associated with a particular risk category, in accordance with one or more embodiments. GUI 600 may be presented in response to a user's selection of risk category 504a of FIG. 5. As illustrated, GUI 600 shows devices that are within a "critical risk" category. In particular, GUI 600 shows the devices in the "critical risk" category by concurrently showing device photos, such as device photo 606, associated with the devices. Each device photo 606 is further associated with a device name 602, a device profile name 604, and an alert icon 606. The device name 602 is a unique name identifying the device. The device profile name 604 is a name of the current device profile determined for the device. The alert icon 606 indicates whether there is an anomalous behavior alert set for the device.

Figure 7:
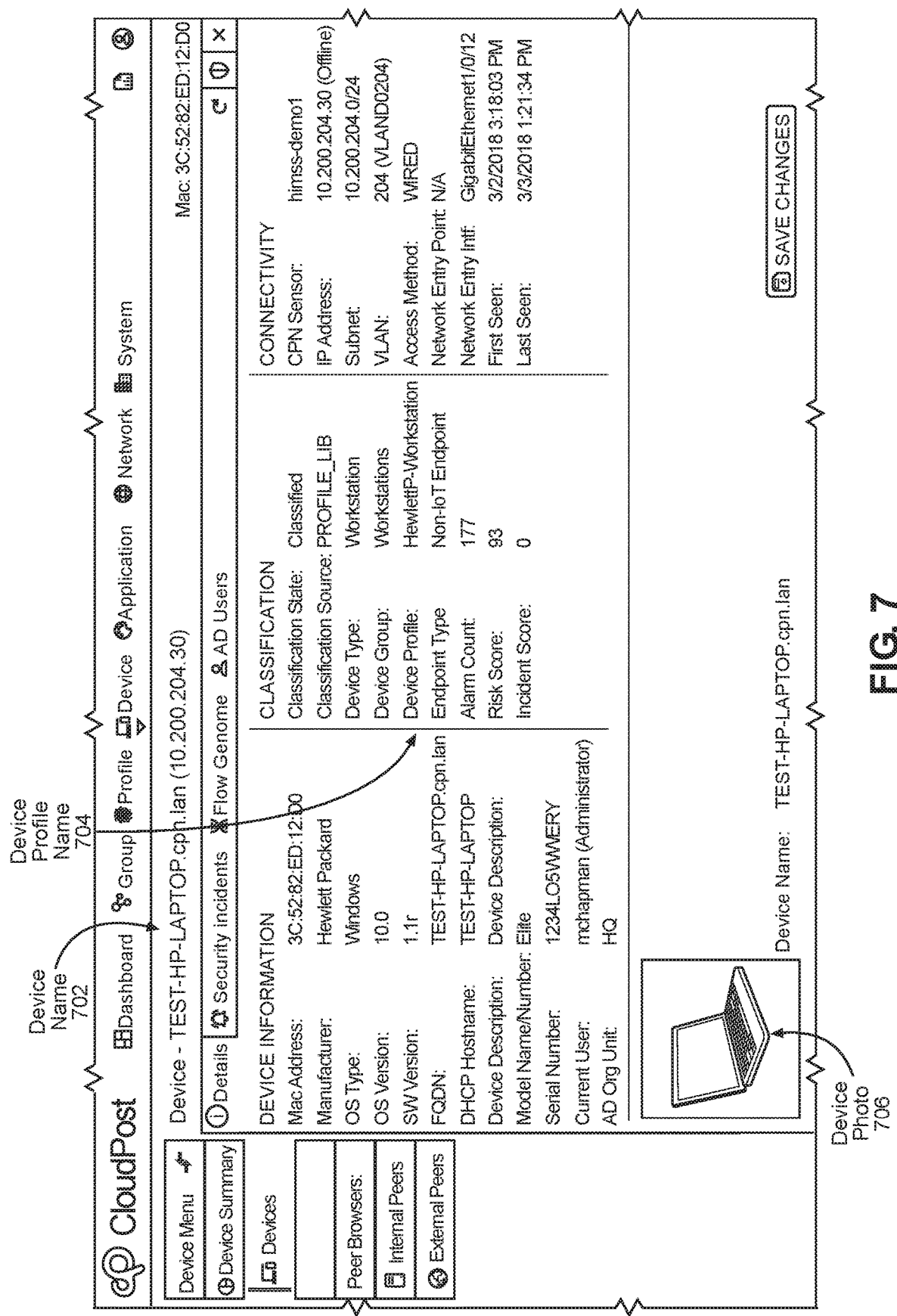
FIG. 7 illustrates an example GUI showing a device photo, a device profile, and additional attributes for a device detected in a network, in accordance with one or more embodiments.

FIG. 7 illustrates an example GUI showing a device photo, a device profile, and additional attributes for a device detected in a network, in accordance with one or more embodiments. GUI 700 may be presented in response to a user's selection of a device shown in GUI 600 of FIG. 6. Alternatively, GUI 700 may be presented in response to a user's selection of a device shown in GUI 400 of FIG. 4.

As illustrated, GUI 700 shows information associated with a particular device with the device name 702, "TEST-HP-LAPTOP.cpn.lan." GUI 700 shows a device profile name 704 for the device, "HewlettP-Workstation." GUI 700 shows a device photo 706 for the device. GUI 700 also shows additional information associated with the device, including MAC address, manufacturer, operating system (OS) type, OS version, software version, Fully Qualified Domain Name (FQDN), DHCP hostname, device description, model name/number, serial number, current user, and Active Directory (AD) organizational unit. GUI 700 also shows additional information associated with a classification of the device, including a classification state (whether a current device profile has been determined for the device), a device type or category of the device, a current device profile for the device, an endpoint type of the device (whether the device is an IoT device or not), an alarm count for the device, a risk score for the device, and an incident score for the device. GUI 700 also shows additional information associated with a connectivity of the device, including an identifier (ID) of a sensor that captured data packets transmitted to or from the device, an IP address of the device, a subnet of the device, a virtual local area network (VLAN) of the device, an access method of the device (wired or wireless), a time at which data packets of the device were first captured by a sensor, and a time at which data packets of the device were last captured by a sensor.

5. DETERMINING ATTRIBUTE VALUES ASSOCIATED WITH A DEVICE

Figure 8:
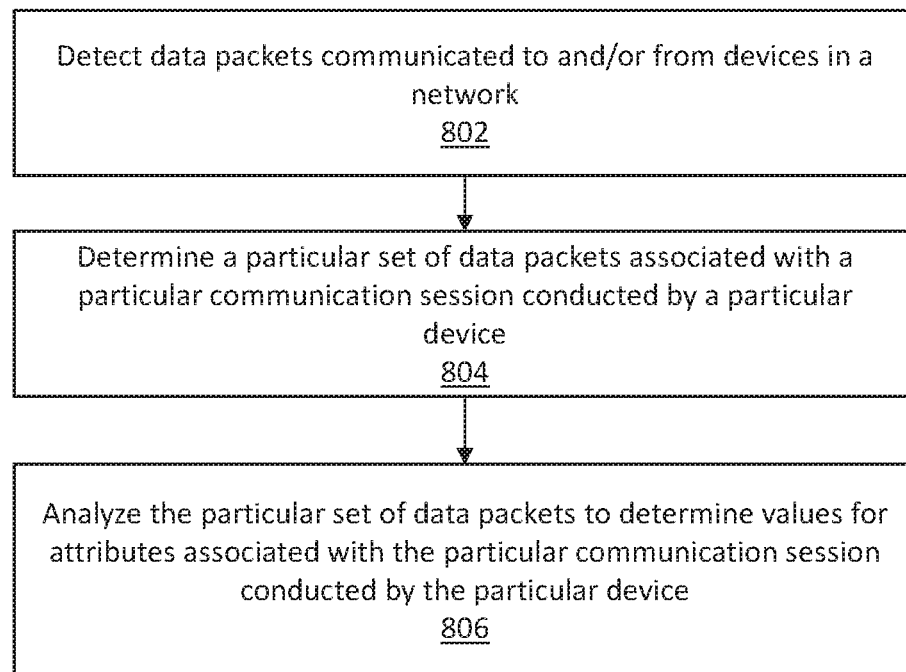
FIG. 8 illustrates an example set of operations for determining attribute values for a communication session conducted by a device in a network, in accordance with one or more embodiments.

FIG. 8 illustrates an example set of operations for determining attribute values for a communication session conducted by a device in a network, in accordance with one or more embodiments. One or more operations illustrated in FIG. 8 may be modified, rearranged, or omitted all together. Accordingly, the particular sequence of operations illustrated in FIG. 8 should not be construed as limiting the scope of one or more embodiments.

One or more embodiments include detecting data packets communicated to and/or from devices in a network (Operation 802). One or more traffic sensors capture data packets communicated in a network, as described above in Section 2, titled "Traffic Sensors in a Network."

One or more embodiments include determining a particular set of data packets associated with a particular communication session conducted by a particular device (Operation 804). Each data packet is analyzed to determine a communication session associated with the data packet.

In an embodiment, a communication session associated with a data packet is determined based on a session ID included in the data packet. Additionally or alternatively, a communication session associated with a data packet is determined based on a source address and a destination address. Data packets transmitted a particular source address and a particular destination address are associated with a same communication session. Additionally or alternatively, a communication session associated with a data packet is determined based on a transmission time of the data packet. Data packets transmitted within a particular time window of each other are associated with a same communication session.

In an embodiment, a device conducting a particular communication session may be identified based on an address and/or ID of the device included in a data packet of the particular communication session. As an example, a source address included in a particular data packet may be 00:2A:10:B9:C8:74. Hence, a device associated with the address 00:2A:10:B9:C8:74 may be determined as conducting a communication session involving the particular data packet. Additionally or alternatively, a device conducting a particular communication session may be identified based on a port used for communicating a data packet. A particular port used for communicating a data packet is determined. A mapping between ports and device IDs may be retrieved from a data repository. Based on the mapping, the particular port may be mapped to a particular device. The particular device may be determined as conducting the communication session.

One or more embodiments include analyzing the particular set of data packets to determine values for attributes associated with the particular communication session conducted by the particular device (Operation 806). A particular set of data packets associated with a same communication session are analyzed to determine attribute values for the communication session. The data packets are parsed, interpreted, and/or analyzed to determine the attribute values.

None, some, or all attribute values may be ascertainable based on the particular set of data packets.

As an example, an x-ray machine may communicate information to a patient database. Data packets transmitted from the x-ray machine may conform to an IPv4 protocol for routing the data packets. The data packets may also include a payload that conforms to a DICOM protocol for communicating medical information. However, the data packets may not use a CIP protocol. Hence, values for flow attributes and DICOM attributes are ascertainable. Values for CIP attributes are not ascertainable.

In an embodiment, each data packet may be parsed to identify different fields and/or components of the data packet. A header, payload, metadata, tail, and/or other component of a data packet may be analyzed.

A header may be parsed to determine attributes associated with IPv4. Based on the IPv4 specification, a field within the data packet for storing an Internet Protocol Version may be identified. A value stored in the field may be determined as the Internet Protocol Version value. The Internet Protocol Version value may be determined as an attribute value for the communication session. Similarly, based on the IPv4 specification, a field within the data packet for storing an Internet Header Length may be identified. A value stored in the field may be determined as the Internet Header Length value. The Internet Header Length value may be determined as another attribute value for the communication session.

A payload may be parsed to determine attributes associated with DICOM (and/or another application protocol). Based on a DICOM specification, a field within the data packet for storing a Consulting Physician's Name may be identified. A value stored in the field may be determined as the Consulting Physician's Name value. The Consulting Physician's Name value may be determined as another attribute value for the communication session.

6. DETERMINING A CURRENT DEVICE PROFILE FOR A DEVICE

Figure 9:
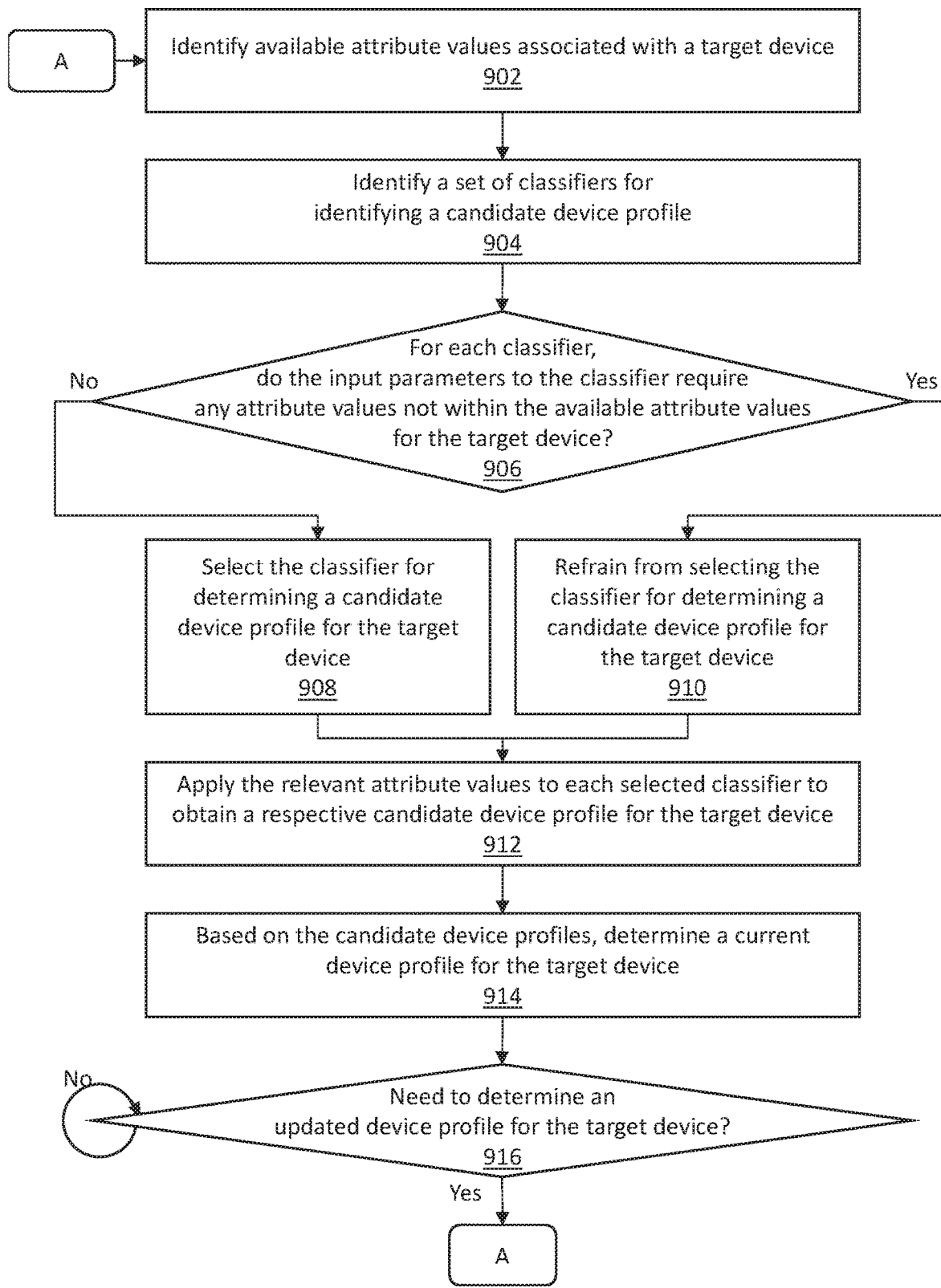
FIG. 9 illustrates an example set of operations for determining a current device profile for a device detected in a network, in accordance with one or more embodiments.

FIG. 9 illustrates an example set of operations for determining a current device profile for a device detected in a network, in accordance with one or more embodiments. One or more operations illustrated in FIG. 9 may be modified, rearranged, or omitted all together. Accordingly, the particular sequence of operations illustrated in FIG. 9 should not be construed as limiting the scope of one or more embodiments.

One or more embodiments include identifying available attribute values associated with a target device (Operation 902). The target device is any device that is detected within a network. Attribute values associated with the target device include attribute values for one or more communication sessions conducted by the target device. Operations illustrated in FIG. 9 may be iterated with respect to each device detected in the network, in order to determine a respective current device profile for each device detected in the network.

First, each detected data packet is analyzed to determine attribute values for the communication session associated with the data packet. Examples of operations for determining attribute values for a communication session are described above with reference to FIG. 8.

Second, each data packet is analyzed to determine an identifier of a device conducting the communication session associated with the data packet. As an example, a data packet may include an identifier of a device conducting the communication session. The data packet may be parsed to extract the identifier of the device conducting the communication session. As another example, a data packet may be analyzed to determine a particular port used for communicating the data packet. A mapping between ports and device identifiers may be retrieved from a data repository. Based on the mapping, the particular port may be mapped to a particular device. The particular device may be determined as conducting the communication session.

Data packets of a set of one or more communication sessions conducted by the same target device are identified. Attribute values for the set of communication sessions are determined as attribute values associated with the target device.

In an embodiment, different data packets refer to the same target device using different identifiers (IDs). The different data packets may use different systems of device identifiers. Additionally or alternatively, the different data packets may be associated with different protocols. A mapping of device identifiers is retrieved and/or obtained from a data repository. The mapping of device identifiers indicates which IDs refer to the same device. Hence, based on the mapping of device identifiers, a set of data packets that refer to the same device are identified. As an example, a DICOM data packet may refer to Device X using the ID 1234, while a POCT data packet may refer to Device X using the ID AG941. An entry in the mapping of identifiers may indicate that both ID 1234 and ID AG941 refer to Device X. Based on the mapping, both the DICOM data packet and the POCT data packet may be determined as referring to the same Device X.

If a particular attribute value is not available for any communications sessions conducted by the target device, then the particular attribute value is determined as unavailable for the target device.

As an example, Data Packet A and Data Packet B are included in Communication Session X, which is conducted by Device V. Data Packet C and Data Packet D are included in Communication Session Y, which is also conducted by Device V. Values for DICOM attributes may be ascertainable and determined based on Data Packet A and Data Packet B. Values for DHCP attributes may be ascertainable and determined based on Data Packet C and Data Packet D. Since both Communication Session X and Communication Session Y are conducted by Device V, available attribute values associated with Device V include the values for the DICOM attributes and the values for the DHCP attributes. However, values for DNS attributes might be unascertainable based on any communication sessions conducted by Device V. Therefore, unavailable attribute values associated with Device V include values for DNS attributes.

One or more embodiments include identifying a set of classifiers for identifying a candidate device profile (Operation 904). A set of classifiers are identified and/or obtained from a data repository. Each classifier is configured to determine a respective candidate device profile for a target device based on a respective set of attribute values associated with the target device.

One or more embodiments include determining whether the input parameters to each classifier require any attribute values not within the available attribute values for the target device (Operation 906). For each classifier, the input parameters to the classifier are identified. The input parameters are compared with the available attribute values associated with the target device. If all input parameters are available, then the input parameters do not require any unavailable attribute values. If one or more input parameters are not available, then the input parameters require unavailable attribute values.

As an example, available attribute values for a target device may include values for BACnet attributes, but not values for RTSP attributes. A set of classifiers may be retrieved from a data repository. A first classifier may require values for BACnet attributes. A second classifier may require values for RTSP attributes. Hence, the first classifier does not require any unavailable attribute values, while the second classifier does require unavailable attribute values.

If a classifier does not require any unavailable attribute values, one or more embodiments include selecting the classifier for determining a candidate device profile for the target device (Operation 908). Classifiers that do not require any unavailable attribute values, as determined at Operation 906, are selected for use.

If a classifier does require one or more unavailable attribute values, one or more embodiments include refraining from selecting the classifier for determining a candidate device profile for the target device (Operation 910). Classifiers that require unavailable attribute values, as determined at Operation 906, are not selected for use.

One or more embodiments include applying the relevant attribute values to each selected classifier to obtain a respective candidate device profile for the target device (Operation 912). For each selected classifier, the attribute values required as input to the classifier are determined. The respective attribute values, determined at Operation 902, are then applied to each selected classifier. Based on the inputted attribute values, each selected classifier outputs a respective candidate device profile for the target device.

As an example, available attribute values for a target device may include values for BACnet attributes, and values for RTSP attributes. A set of classifiers may be retrieved from a data repository. A first classifier may require values for BACnet attributes. A second classifier may require values for RTSP attributes. Hence, the BACnet attribute values are inputted to the first classifier. The first classifier outputs a candidate device profile baesd on the BACnet attribute values. The RTSP attribute values are inputted to the second classifier. The second classifier outputs a candidate device profile baesd on the RTSP attribute values.

One or more embodiments include determining a current device profile for the target device based on the candidate device profiles (Operation 914).

A profile score is determined for each candidate device profile outputted from a selected classifier. First, respective weights corresponding to the selected classifiers are retrieved and/or obtained from a data repository. The weight, corresponding to a particular classifier, is applied to the candidate device profile output from the particular classifier. Then for each candidate device profile, a profile score is determined based on the weights. The profile score may be, for example, the sum of weights corresponding to the candidate device profile. The candidate device profile with the greatest profile score is determined as a current device profile for the target device. Additional or alternative methods for applying weights to the candidate device profiles outputted from the selected classifiers may also be used.

As an example, a candidate device profile determined by a first classifier may be "medical device." A candidate device profile determined by a second classifier may also be "medical device." A candidate device profile determined by a third classifier may be "media device."

The first classifier may be associated with a weight of 1. The second classifier may be associated with a weight of 1. The third classifier may be associated with a weight of 3.

Hence, a summary of the classifiers, candidate device profiles, and weights may be as follows:

| Classifier | Candidate Device Profile | Weight |
| --- | --- | --- |
| First Classifier | Medical Device | 1 |
| Second Classifier | Medical Device | 1 |
| Third Classifier | Media Device | 3 |

A profile score for a candidate device profile may be the sum of weights corresponding to the candidate device profile. Hence, a profile score for the "medical device" profile is 1+1=2. A profile score for the "media device" profile is 3. Therefore, the candidate device profile associated with the greatest profile score is the "media device" profile. Hence, the "media device" profile may be determined as a current device profile for the device.

In an embodiment, equal weights correspond to all classifiers. Hence, a simple majority vote is used to determine a current device profile. A number of classifiers that output each candidate device profile is determined. The candidate device profile that is determined by the largest number of classifiers is identified. The identified candidate device profile is determined as a current device profile for the target device.

Additional or alternative methods for determining a current device profile for the target device based on the candidate device profiles may also be used.

In an embodiment, the weights associated with the selected classifiers are used to determine a confidence level associated with the determination of the current device profile. As described above, a candidate device profile associated with the greatest profile score may be determined as a current device profile. The confidence level associated with the determination of the current device profile may be determined in various ways. In an example, a confidence level associated with the determination of the current device profile is directly proportional to the profile score for the current device profile. In another example, a profile score for each candidate device profile is determined. A confidence level associated with the determination of the current device profile is determined based on a distribution of the respective profile scores for the candidate device profiles. The greater the difference between (a) the profile score for the current device profile and (b) the profile scores for the remaining candidate device profiles, the greater the confidence level. The lesser the difference between (a) the profile score for the current device profile and (b) the profile scores for the remaining candidate device profiles, the lesser the confidence level.

One or more embodiments include determining whether there is a need to determine an updated device profile for the target device (Operation 916). An updated device profile for the target device may be determined on a periodic basis, such as once per day, or once per week. An updated device profile may hence be needed at the scheduled time. Additionally or alternatively, an updated device profile for the target device may be determined based on a triggering event. The triggering event may be, for example, the detection of additional available attribute values associated with the target device.

7. PRESENTING, AT A GUI, DEVICE PHOTOS AND ASSOCIATED INFORMATION FOR DEVICES DETECTED IN A NETWORK

Figure 10A:
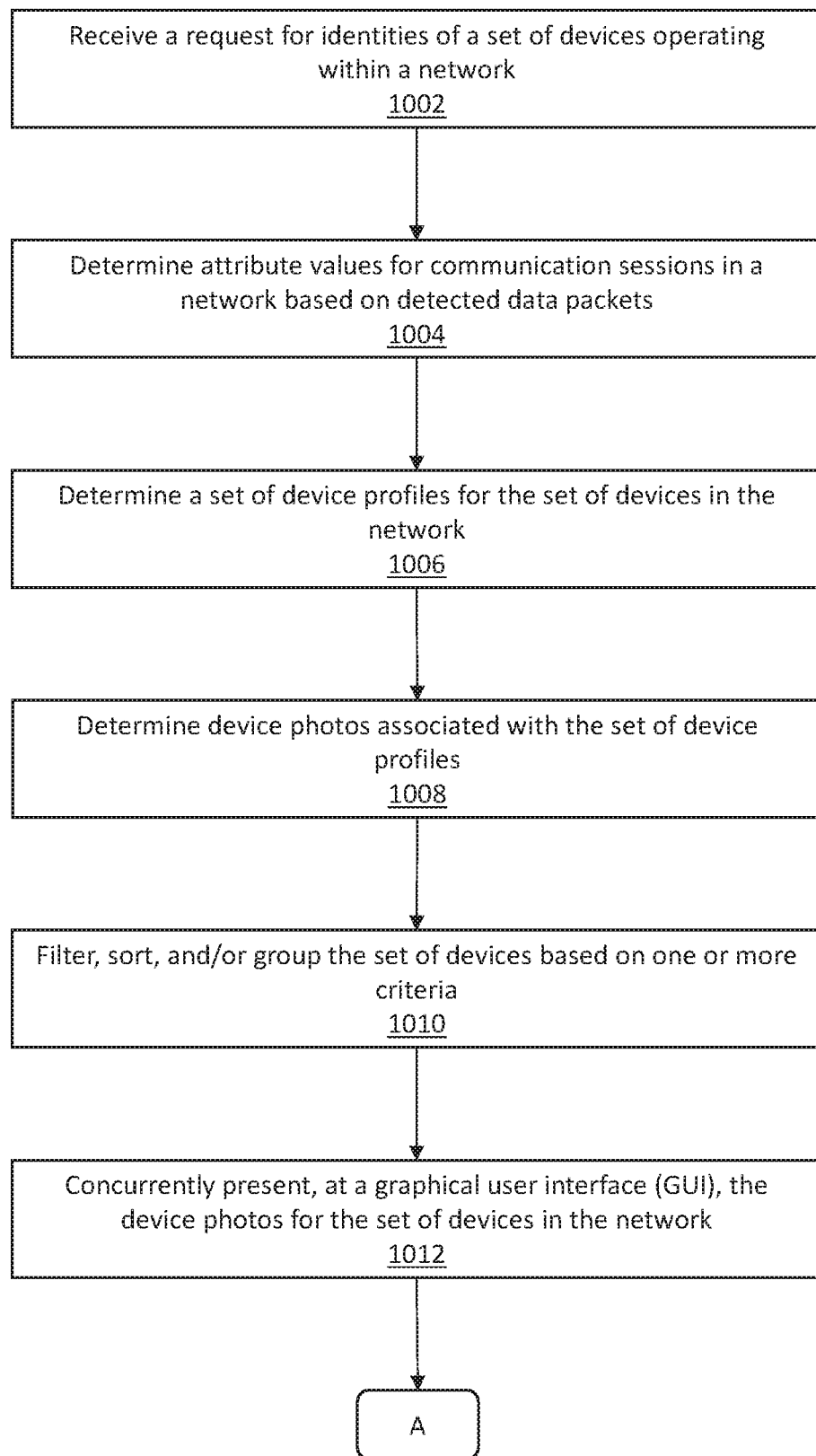
FIGS. 10A-B illustrate an example set of operations for presenting, at a GUI, device photos and associated information for devices detected in a network, in accordance with one or more embodiments.
Figure 10B:
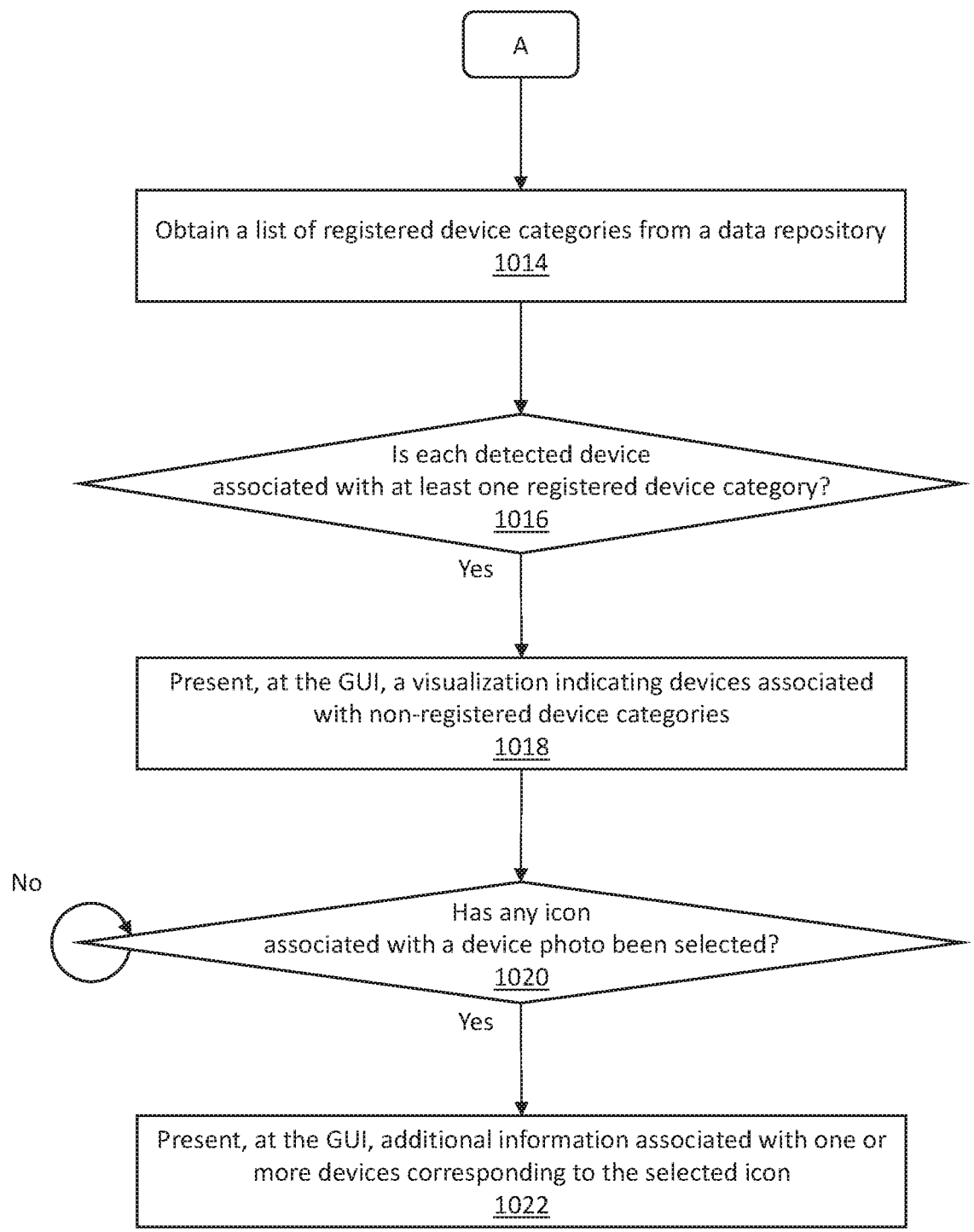

FIGS. 10A-B illustrate an example set of operations for presenting, at a GUI, device photos and associated information for devices detected in a network, in accordance with one or more embodiments. One or more operations illustrated in FIGS. 10A-B may be modified, rearranged, or omitted all together. Accordingly, the particular sequence of operations illustrated in FIGS. 10A-B should not be construed as limiting the scope of one or more embodiments.

One or more embodiments include receiving a request for identities of a set of devices operating within a network (Operation 1002). A GUI presents an interface element configured to a request for identities of a set of devices operating within a network. The GUI receives, via the interface element, the request for identities of the set of devices operating within the network.

One or more embodiments include determining attribute values for communication sessions in a network based on detected data packets (Operation 1004). Examples of operations for determining attribute values for a communication session conducted by a device in a network are described above with reference to FIG. 8.

One or more embodiments include determining a set of device profiles for the set of devices in the network (Operation 1006). Examples of operations for determining a device profile for a device are described above with reference to FIG. 9.

In an embodiment, each data packet is analyzed to determine one or more of: a device that transmitted the data packet, and a device that received the data packet. The set of devices communicating in the network include any device identified as transmitting and/or receiving a detected data packet. A set of devices that transmit and/or receive one or more data packets detected in the network may also be referred to herein as a "set of devices detected in a network." Hence, a set of devices communicating in a network is identified based on the detected data packets.

In an embodiment, attribute values associated with each device in the network are determined based on the data packets transmitted and/or received by the device. The attribute values are used for determining a device profile for the device. As an example, a device profile may be determined by inputting the attribute values to classifiers, as described above with reference to FIG. 9. As another example, a table may map attribute values to device profiles. Based on the table, the detected attribute values for a particular device may be mapped to a particular device profile. The particular device profile is determined as a current device profile for the particular device. Additional or alternative methods for determining a device profile for a device may also be used.

One or more embodiments include determining device photos associated with the set of device profiles (Operation 1008). As described above with reference to FIG. 3, each device profile is associated with a device photo. Based on the device profiles determined for the set of devices in the network at Operation 1006, the device photos associated with the device profiles are identified.

One or more embodiments include filtering, sorting, and/or grouping the set of devices based on one or more analysis criteria (Operation 1010). The set of devices in the network are filtered, sorted, and/or grouped based on one or more analysis criteria.

As an example, an analysis criteria may be device categories. In particular, a respective device category associated with each device is determined based on a device profile determined for each device. Devices are filtered, sorted, and/or grouped based on the respective device categories associated with the devices. For example, all devices in a medical device category may be grouped together; all devices in a media device category may be grouped together; all devices in an appliances category may be grouped together.

As another example, an analysis criteria may be risk scores. Examples of operations for determining a risk score for a device are described below with reference to FIG. 11. Devices are filtered, sorted, and/or grouped based on the respective risk scores associated with the devices. For example, devices associated with higher risk scores (indicating higher level of risk) may be sorted to appear first, while devices associated with lower risk scores may be sorted to appear last.

As another example, an analysis criteria may be address categories. In particular, data packets transmitted to a device are analyzed to determine a source network addresses. Data packets transmitted from a device are analyzed to determine a destination network address. An address category is determined for each source network addresses and/or each destination network addresses. Devices communicating with network addresses of certain address categories (such as, communicating with only internal network addresses) may be filtered out.

Additional or alternative criteria for filtering, sorting, and/or grouping the devices may be used.

One or more embodiments include concurrently presenting, at a graphical user interface (GUI), the device photos for the set of devices in the network (Operation 1012). A GUI concurrently presents the device photos for the set of devices. Referring to FIG. 4 as described above, FIG. 4 illustrates an example GUI showing device photos of devices detected in a network, in accordance with one or more embodiments. Hence, a user may easily identify the devices in the network in pictorial form.

The GUI may present the device photos based on a filtering, sorting, and/or grouping of the devices determined at Operation 1010.

As an example, all devices in a medical device category may be grouped together; all devices in a media device category may be grouped together; all devices in an appliances category may be grouped together. Hence, a single device photo represents the medical device category; a single device photo represents the media device category; a single device photo represents the appliance category. A GUI may concurrently present: a photo representing the medical device category, a photo representing the media device category, and a photo representing the appliance category. Hence, a user may easily view the device categories that are present in a network. A user may easily identify any device categories that should not be present in a network.

As another example, devices associated with higher risk scores (indicating higher level of risk) may be sorted to appear first, while devices associated with lower risk scores may be sorted to appear last. Hence, a GUI may concurrently present a device photo for each device. The device photos may be ordered such that the devices associated with the higher risk scores are presented first in a list, while devices associated with lower risk scores are presented last in the list. Hence, a user may easily identify the devices associated with the highest risk scores, and resolve any risk issues accordingly.

As another example, devices communicating with only internal network addresses may be filtered out. A GUI may concurrently present a device photo for each device that is not filtered out. Hence, the GUI may concurrently present a device photo for each device that communicates with at least one external network address. The GUI does not present any device photo for a device that communicates with only internal network addresses. Hence, a user may focus on analyzing devices communicating with external network addresses, without manually skipping through devices communicating with only internal network addresses.

One or more embodiments include obtaining a list of registered device categories from a data repository (Operation 1014). A list of registered device categories may be retrieved and/or obtained from a data repository. The list of registered device categories may be compiled and/or generated based on user input. As an example, one or more users may input and/or upload registered device categories.

One or more embodiments include determining whether each detected device is associated with at least one registered device category (Operation 1016). A device category associated with each device is determined. The device category associated with a device is indicated by the device profile determined, at Operation 1006, for the device. The device category associated with the device is compared to the list of registered device categories. If the device category associated with the device is on the list of registered device categories, then the detected device is associated with a registered device category. If the device category associated with the device is not on the list of registered device categories, then the detected device is not associated with a registered device category.

One or more embodiments include presenting, at the GUI, a visualization indicating devices associated with non-registered device categories (Operation 10). As the GUI concurrently presents the device photos at Operation 1002, the GUI also presents a visualization indicating devices associated with non-registered device categories.

As an example, the GUI may present a box or another shape around device photos for devices associated with non-registered device categories. As another example, the GUI may present device photos for devices associated with non-registered device categories using a particular color shading. As another example, the GUI may cause present device photos for devices associated with non-registered device categories to flash, or another animation may be used.

Additional or alternative visualizations indicating devices associated with non-registered device categories may also be used.

One or more embodiments include determining whether any icon associated with a device photo has been selected (Operation 1020). The GUI presents an icon associated with each device photo. An icon may be the device photo itself. Additionally or alternatively, an icon may be separate from the device photo, such as a button adjacent to the device photo.

The GUI is configured to receive user selection of one or more icons. As an example, a user may use a mouse to click on an icon. As another example, a user may use a keyboard to indicate a selection of an icon. As another example, a user may use a voice command to indicate a selection of an icon.

One or more embodiments include presenting, at the GUI, additional information associated with one or more devices corresponding to the selected icon (Operation 1022). In response to a selection of an icon, the GUI presents additional information associated with one or more devices corresponding to the device photo of the selected icon. Additional information associated with a device may include any information described above with reference to FIG. 7. Additionally or alternatively, additional information associated with a device may include other information associated with the device, which is not necessarily described with reference to FIG. 7.

As an example, a GUI may present a device photo for each device detected in a network. A user may select an icon associated with a particular device photo, which represents a particular device. In response, the GUI may present additional information associated with the particular device.

As another example, devices may be grouped by device category, and a GUI may present a single photo representing each device category. A user may select an icon associated with a particular device photo, which represents a particular device category. In response, the GUI may present additional information associated with a set of devices associated with the particular device category.

As another example, devices may be grouped by device category, and a GUI may present a single photo representing each device category. A user may select an icon associated with a particular device photo, which represents a particular device category. In response, the GUI may present another set of device photos, each device photo associated with a device in the particular device category. A user may select another icon associated with another device photo, which represents a particular device. In response, the GUI may present additional information associated with the particular device.

8. DETERMINING A RISK CATEGORY AND/OR ANOMALOUS BEHAVIOR FOR A DEVICE

Figure 11:
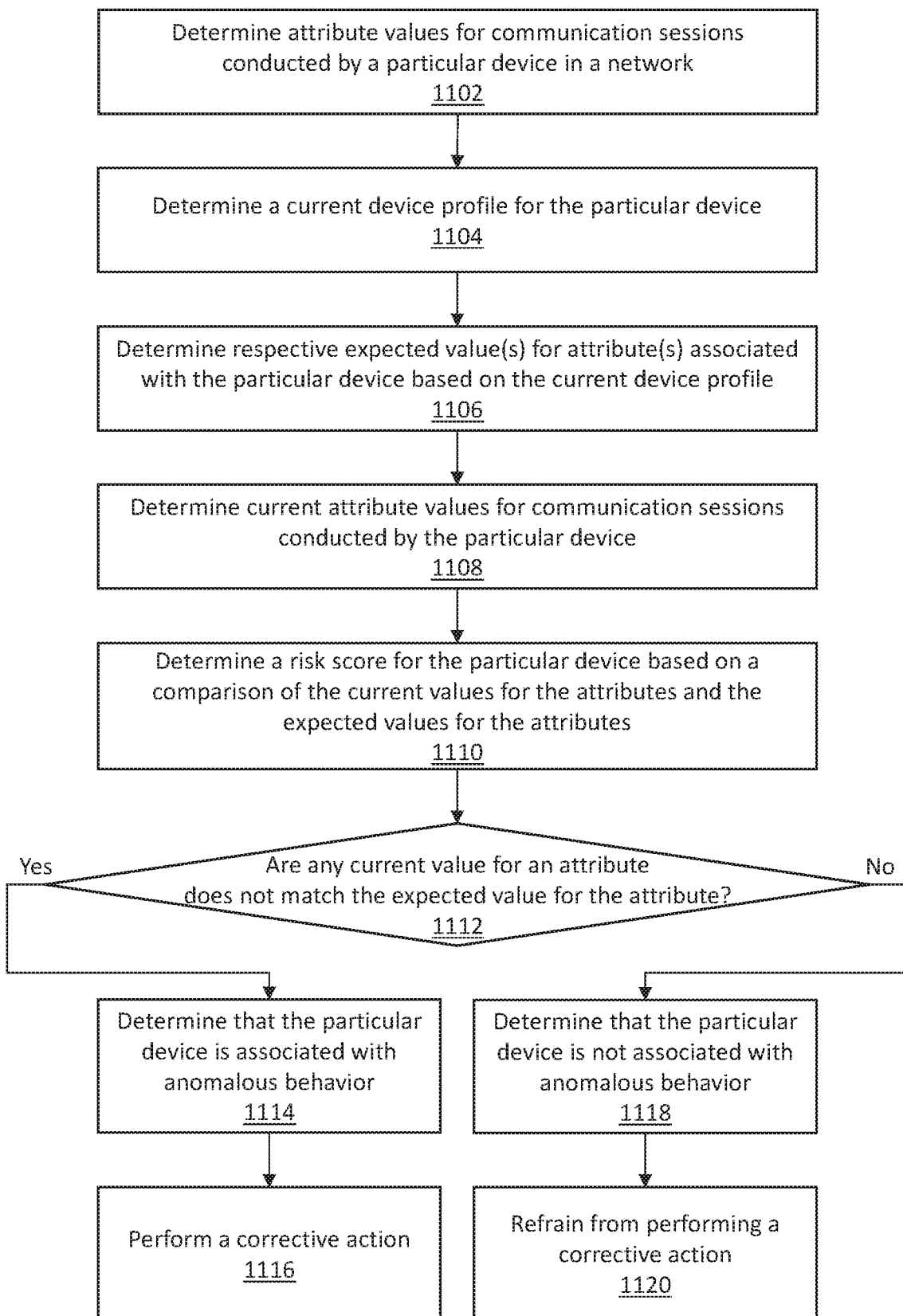
FIG. 11 illustrates an example set of operations for determining a risk category and/or anomalous behavior of a device detected in a network, in accordance with one or more embodiments.

FIG. 11 illustrates an example set of operations for determining a risk category and/or anomalous behavior for a device detected in a network, in accordance with one or more embodiments. One or more operations illustrated in FIG. 11 may be modified, rearranged, or omitted all together. Accordingly, the particular sequence of operations illustrated in FIG. 11 should not be construed as limiting the scope of one or more embodiments.

One or more embodiments include determining attribute values for communication sessions conducted by a particular device in a network (Operation 1102). Examples of operations for determining attribute values for a communication session conducted by a device in a network are described above with reference to FIG. 8. Examples of operations for identifying available attribute values associated with a particular device are described above with reference to Operation 902 of FIG. 9.

One or more embodiments include determining a current device profile for the particular device (Operation 1104). Examples of operations for determining a device profile for a device are described above with reference to FIG. 9.

One or more embodiments include determining respective expected value(s) for one or more attributes associated with the particular device based on the current device profile (Operation 1106). Expected attribute values are indicated by the current device profile for the device. As an example, a particular device profile may indicate that the expected values for a Consulting Physician's Name attribute in a DICOM data packet include: John Smith, Ada Wong, and Henry Seto. A particular device in a network may be determined as being associated with the particular device profile. Hence, based on the particular device profile, the expected values for the Consulting Physician's Name attribute for the particular device include: John Smith, Ada Wong, and Henry Seto.

One or more embodiments include determining current attribute values for communication sessions conducted by the particular device (Operation 1108). Examples of operations for determining attribute values for a communication session conducted by a device in a network are described above with reference to FIG. 8. Examples of operations for identifying available attribute values associated with a particular device are described above with reference to Operation 902 of FIG. 9.

The attribute values determined at Operation 1102 and the attribute values determined at Operation 1108 may be the same or different.

In an embodiment, a set of data packets are detected and used for determining the attribute values at Operation 1102. The attribute values are used for determining a current device profile for the device. The current device profile indicates a set of expected values for the attributes. The same attribute values determined at Operation 1102 are used as the current attribute values at Operation 1108. The current attribute values are compared to the expected attribute values, as further described below at Operation 110.

In an embodiment, a set of data packets are detected and used for determining the attribute values at Operation 1102. The attribute values are used for determining a current device profile for the device. The current device profile indicates a set of expected values for the attributes. Another set of data packets are detected and used for determining the current attribute values at Operation 1108. The current attribute values are compared to the expected attribute values, as further described below at Operation 110.

One or more embodiments include determining a risk score for the particular device based on a comparison of the current values for the attributes and the expected values for the attributes (Operation 1110). The current value for each attribute is compared to the expected value for the attribute to compute a respective disparity score. The disparity scores associated with the attributes are aggregated to determine a risk score.

In an embodiment, an attribute value is a numerical value. A difference between the current value for the attribute and the expected value for the attribute is computed. A disparity score associated with the attribute is determined based on the difference. As an example, the difference may be normalized to compute the disparity score.

In an embodiment, an attribute value is not a numerical value. If the current value for the attribute and the expected value for the attribute are the same, then the disparity score associated with the attribute may be determined as a first value (such as, zero). If the current value for the attribute and the expected value for the attribute are different, then the disparity score associated with the attribute may be determined as a second value (such as, one).

In an embodiment, each attribute is associated with a weight. The weight is applied to the respective disparity score. The weighted disparity scores are aggregated to compute the risk score. A greater weight associated with a particular attribute indicates that greater significance is given to the disparity score for the particular attribute. A lesser weight associated with a particular attribute indicates that lesser significance is given to the disparity score for the particular attribute.

As an example, a particular BACnet attribute may be associated with a weight of 0.8. A particular flow attribute may be associated with a weight of 0.4.

A disparity score associated with the particular BACnet attribute may be determined as 0.5. A disparity score associated with the particular flow attribute may be determined as 0.6.

For the BACnet attribute, the weight of 0.8 may be applied to the disparity score of 0.5 to obtain 0.8×0.5=0.40.

For the flow attribute, the weight of 0.4 may be applied to the disparity score of 0.6 to obtain 0.4×0.6=0.24.

Hence, a risk score may be computed as 0.40+0.24=0.64.

In the above example, the disparity score associated with the BACnet attribute is lesser than the disparity score associated with the flow attribute. However, after application of the weights, the significance given to the disparity score associated with the BACnet attribute is greater than the significance given to the disparity score associated with the flow attribute.

In an embodiment, a risk score for the particular device is adjusted and/or determined based on a confidence level associated with the determination of the current device profile for the particular device. Examples of operations for determining a confidence level are described above with reference to Operation 914 of FIG. 9. A risk score may be increased based on a greater level of confidence. Additionally or alternatively, a risk score may be decreased based on a lesser level of confidence. As an example, a disparity score may be computed for each attribute. An aggregated disparity score may be computed. The aggregated disparity score may be multiplied by the confidence level associated with the determination of the current device profile. The resulting product may be determined as the risk score for the device.

Additional or alternative methods for determining a risk score based on a comparison of the current attribute values and the expected attribute values may be used.

One or more embodiments include determining whether any current value for an attribute does not match the expected value for the attribute (Operation 1112). The current value for each attribute is compared to the expected value for the attribute.

In an embodiment, an attribute is associated with a range of expected values, and/or a set of expected values. If the current attribute value is within the range of expected values, or if the current attribute value is one of the set of expected values, then the current attribute value is determined as matching the expected attribute value. Conversely, if the current attribute value is not within the range of expected values, or if the current attribute value is not one of the set of expected values, then the current attribute value is determined as not matching the expected attribute value.

In an embodiment, an attribute is associated with a single expected value. If the current attribute value is the same as the expected attribute value, then the current attribute value is determined as matching the expected attribute value. Conversely, if the current attribute value is not the same as the expected attribute value, then the current attribute value is determined as not matching the expected attribute value.

In an embodiment, an attribute is expected to have a null value. If the value for the attribute is not ascertainable, then the current attribute value is determined as matching the expected attribute value. Conversely, if there is a value determined for the attribute, then the current attribute value is determined as not matching the expected attribute value.

If a current value does not match the expected value for an attribute, one or more embodiments include determining that the particular device is associated with anomalous behavior (Operation 1114). One or more embodiments include performing a corrective action (Operation 1116).

In an embodiment, a corrective action is to provide an anomalous behavior alert. A GUI presents an anomalous behavior alert. In response to the anomalous behavior alert, a user and/or another application may perform additional actions. For example, a user may physically remove the particular device performing the anomalous behavior from the network.

In an embodiment, a corrective action is to disconnect the particular device performing the anomalous behavior from the network. Additionally or alternatively, a corrective action is to prohibit the particular device from connecting to the network. The corrective action may include refusing to authenticate the device to the network. The corrective action may include refraining from routing and/or forwarding data packets transmitted to and/or from the device.

In an embodiment, a corrective action is to quarantine the particular device performing the anomalous behavior from the network. The device may be permitted to remain connected to the network. However, instead of transmitting data packets from the device to a destination address as intended, the data packets may be re-routed to an analysis engine to analyze the data packets. Additionally or alternatively, instead of transmitting data packets to the device as intended, the data packets may be re-routed to an analyze engine to analyze the data packets. The data packets may be analyzed to further understand the anomalous behavior, such as the cause of the anomalous behavior, the actors involved in the anomalous behavior, and/or other characteristics of the anomalous behavior.

Additional or alternative corrective actions may also be performed.

If current values match the expected values for the attributes, one or more embodiments include determining that the particular device is not associated with anomalous behavior (Operation 1118). One or more embodiments include refraining from performing a corrective action (Operation 1120). The particular device may be permitted to continue operating as normal.

9. PRESENTING, AT A GUI, RISK CATEGORIES AND ASSOCIATED INFORMATION FOR DEVICES DETECTED IN A NETWORK

Figure 12:
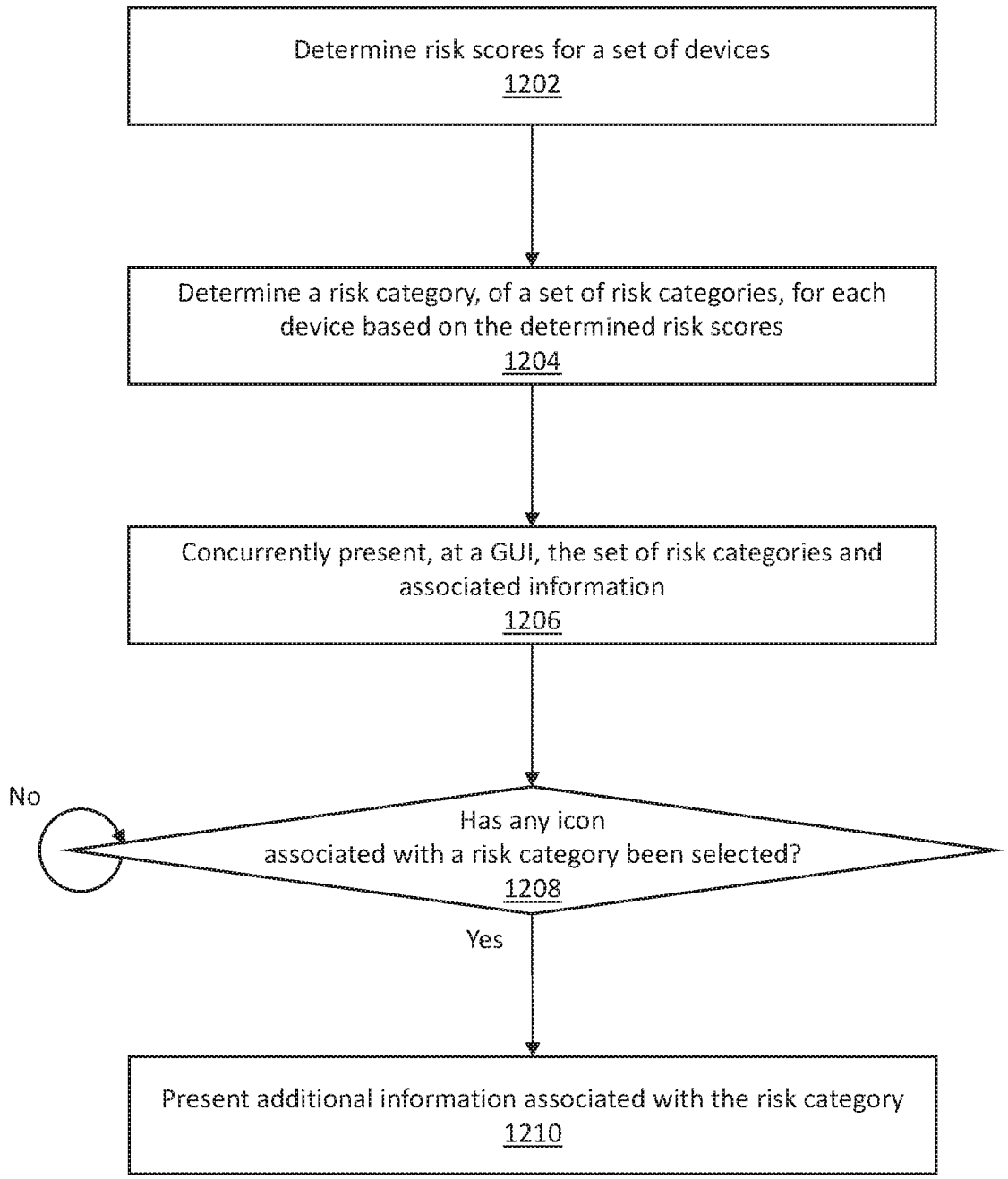
FIG. 12 illustrates an example set of operations for presenting, at a GUI, risk categories and associated information for devices detected in a network, in accordance with one or more embodiments.

FIG. 12 illustrates an example set of operations for presenting, at a GUI, risk categories and associated information for devices detected in a network, in accordance with one or more embodiments. One or more operations illustrated in FIG. 12 may be modified, rearranged, or omitted all together. Accordingly, the particular sequence of operations illustrated in FIG. 12 should not be construed as limiting the scope of one or more embodiments.

One or more embodiments include determining risk scores for a set of devices (Operation 1202). Examples of operations for determining a risk score for a device are described above with reference to FIG. 11, and in particular Operation 1110.

One or more embodiments include determining a risk category, of a set of risk categories, for each device based on the determined risk scores (Operation 1204). A respective range of risk scores associated with each risk category is retrieved and/or obtained from a data repository. The risk score associated with each device is compared with the range of risk scores associated with each risk category. If a risk score associated with a device falls within the range of risk scores associated with a particular risk category, then the particular risk category is determined for the device.

As an example, ranges of risk scores associated with risk categories include:
(a) critical risk: 0.76-1.00;
(b) high risk: 0.51-0.75;
(c) medium risk: 0.26-0.50;
(d) low risk: 0.11-0.25;
(e) normal (no risk): 0-0.10.

A risk score determined for Device X may be 0.82. Since the risk score of 0.82 falls within the range of 0.76-1.00, Device X is determined as being associated with the critical risk category.

A risk score determined for Device Y may be 0.15. Since the risk score of 0.15 falls within the range of 0.11-0.25, Device Y is determined as being associated with the low risk category.

One or more embodiments include concurrently presenting, at a GUI, a set of risk categories and associated information (Operation 1206). A GUI concurrently presents a set of risk categories. The GUI also presents information associated with each risk category, such as a number of devices categorized into each risk category. Referring to FIG. 5 as described above, FIG. 5 illustrates an example GUI showing risk categories and associated information, in accordance with one or more embodiments.

One or more embodiments include determining whether any icon associated with a risk category has been selected (Operation 1208). The GUI presents an icon associated with each risk category. An icon may be the risk category itself. Additionally or alternatively, an icon may be separate from the risk category, such as a button adjacent to the risk category.

The GUI is configured to receive user selection of one or more icons. As an example, a user may use a mouse to click on an icon. As another example, a user may use a keyboard to indicate a selection of an icon. As another example, a user may use a voice command to indicate a selection of an icon.

One or more embodiments include presenting additional information associated with the risk category (Operation 1210). In response to a selection of an icon, the GUI presents additional information associated with one or more devices corresponding to the risk category of the selected icon. Additional information associated with a device may include any information described above with reference to FIG. 7. Additionally or alternatively, additional information associated with a device may include other information associated with the device, which is not necessarily described with reference to FIG. 7.

10. HARDWARE OVERVIEW

According to one embodiment, the techniques described herein are implemented by one or more special-purpose computing devices. The special-purpose computing devices may be hard-wired to perform the techniques, or may include digital electronic devices such as one or more application-specific integrated circuits (ASICs), field programmable gate arrays (FPGAs), or network processing units (NPUs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, FPGAs, or NPUs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 13 is a block diagram that illustrates a computer system 1300 upon which an embodiment of the invention may be implemented. Computer system 1300 includes a bus 1302 or other communication mechanism for communicating information, and a hardware processor 1304 coupled with bus 1302 for processing information. Hardware processor 1304 may be, for example, a general purpose microprocessor.

Computer system 1300 also includes a main memory 1306, such as a random access memory (RAM) or other dynamic storage device, coupled to bus 1302 for storing information and instructions to be executed by processor 1304. Main memory 1306 also may be used for storing temporary variables or other intermediate information during execution of instructions to be executed by processor 1304. Such instructions, when stored in non-transitory storage media accessible to processor 1304, render computer system 1300 into a special-purpose machine that is customized to perform the operations specified in the instructions.

Computer system 1300 further includes a read only memory (ROM) 1308 or other static storage device coupled to bus 1302 for storing static information and instructions for processor 1304. A storage device 1310, such as a magnetic disk or optical disk, is provided and coupled to bus 1302 for storing information and instructions.

Computer system 1300 may be coupled via bus 1302 to a display 1312, such as a cathode ray tube (CRT), for displaying information to a computer user. An input device 1314, including alphanumeric and other keys, is coupled to bus 1302 for communicating information and command selections to processor 1304. Another type of user input device is cursor control 1316, such as a mouse, a trackball, or cursor direction keys for communicating direction information and command selections to processor 1304 and for controlling cursor movement on display 1312. This input device typically has two degrees of freedom in two axes, a first axis (e.g., x) and a second axis (e.g., y), that allows the device to specify positions in a plane.

Computer system 1300 may implement the techniques described herein using customized hard-wired logic, one or more ASICs or FPGAs, firmware and/or program logic which in combination with the computer system causes or programs computer system 1300 to be a special-purpose machine. According to one embodiment, the techniques herein are performed by computer system 1300 in response to processor 1304 executing one or more sequences of one or more instructions contained in main memory 1306. Such instructions may be read into main memory 1306 from another storage medium, such as storage device 1310. Execution of the sequences of instructions contained in main memory 1306 causes processor 1304 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 1310. Volatile media includes dynamic memory, such as main memory 1306. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, content-addressable memory (CAM), and ternary content-addressable memory (TCAM).

Storage media is distinct from but may be used in conjunction with transmission media. Transmission media participates in transferring information between storage media. For example, transmission media includes coaxial cables, copper wire and fiber optics, including the wires that comprise bus 1302. Transmission media can also take the form of acoustic or light waves, such as those generated during radio-wave and infra-red data communications.

Various forms of media may be involved in carrying one or more sequences of one or more instructions to processor 1304 for execution. For example, the instructions may initially be carried on a magnetic disk or solid state drive of a remote computer. The remote computer can load the instructions into its dynamic memory and send the instructions over a telephone line using a modem. A modem local to computer system 1300 can receive the data on the telephone line and use an infra-red transmitter to convert the data to an infra-red signal. An infra-red detector can receive the data carried in the infra-red signal and appropriate circuitry can place the data on bus 1302. Bus 1302 carries the data to main memory 1306, from which processor 1304 retrieves and executes the instructions. The instructions received by main memory 1306 may optionally be stored on storage device 1310 either before or after execution by processor 1304.

Computer system 1300 also includes a communication interface 1318 coupled to bus 1302. Communication interface 1318 provides a two-way data communication coupling to a network link 1320 that is connected to a local network 1322. For example, communication interface 1318 may be an integrated services digital network (ISDN) card, cable modem, satellite modem, or a modem to provide a data communication connection to a corresponding type of telephone line. As another example, communication interface 1318 may be a local area network (LAN) card to provide a data communication connection to a compatible LAN. Wireless links may also be implemented. In any such implementation, communication interface 1318 sends and receives electrical, electromagnetic or optical signals that carry digital data streams representing various types of information.

Network link 1320 typically provides data communication through one or more networks to other data devices. For example, network link 1320 may provide a connection through local network 1322 to a host computer 1324 or to data equipment operated by an Internet Service Provider (ISP) 1326. ISP 1326 in turn provides data communication services through the world wide packet data communication network now commonly referred to as the "Internet" 1328. Local network 1322 and Internet 1328 both use electrical, electromagnetic or optical signals that carry digital data streams. The signals through the various networks and the signals on network link 1320 and through communication interface 1318, which carry the digital data to and from computer system 1300, are example forms of transmission media.

Computer system 1300 can send messages and receive data, including program code, through the network(s), network link 1320 and communication interface 1318. In the Internet example, a server 1330 might transmit a requested code for an application program through Internet 1328, ISP 1326, local network 1322 and communication interface 1318.

The received code may be executed by processor 1304 as it is received, and/or stored in storage device 1310, or other non-volatile storage for later execution.

11. MISCELLANEOUS; EXTENSIONS

Embodiments are directed to a system with one or more devices that include a hardware processor and that are configured to perform any of the operations described herein and/or recited in any of the claims below.

In an embodiment, a non-transitory computer readable storage medium comprises instructions which, when executed by one or more hardware processors, causes performance of any of the operations described herein and/or recited in any of the claims.

Any combination of the features and functionalities described herein may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A non-transitory computer readable medium comprising instructions which, when executed by one or more hardware processors, cause performance of operations comprising:
    obtaining a first set of one or more data packets associated with a communication session conducted by a first device in a network;
    determining a first value for a first attribute associated with the first device based on the first set of data packets;
    determining a second value for a second attribute associated with the first device based on the first set of data packets;
    determining that any value for a third attribute associated with the first device has not been determined based on the first set of data packets;
    selecting a subset of a set of classifiers, wherein the subset of classifiers:
        includes a first classifier that is associated with the first attribute;
        includes a second classifier that is associated with the second attribute;
        does not include a third classifier that is associated with the third attribute;
    applying at least the first value for the first attribute to the first classifier to determine a first candidate device profile, of a plurality of candidate device profiles, for the first device;
    applying at least the second value for the second attribute to the second classifier to determine a second candidate device profile, of the plurality of candidate device profiles, for the first device;
    refraining from using the third classifier to determine any candidate device profile for the first device;
    based at least on the first candidate device profile and the second candidate device profile, determining the first candidate device profile as a current device profile for the first device;
    wherein determining the first candidate device profile as the current device profile for the first device comprises:
        determining a first weight associated with the first classifier;
        determining a second weight associated with the second classifier;
        determining a first profile score for the first candidate device profile based at least on the first weight;
        determining a second profile score for the second candidate device profile based at least on the second weight;
        determining that the first profile score is greater than the second profile score;
    determining one or more expected values for the first attribute based on the current device profile;
    determining whether a particular value for the first attribute matches the one or more expected values for the first attribute;
    responsive to determining that the particular value for the first attribute does not match the one or more expected values for the first attribute: performing a corrective action.

2. The medium of claim 1, wherein the operations further comprise:
    subsequent to determining the current device profile for the first device:
    obtaining a second set of one or more data packets associated with a second communication session conducted by the first device;
    determining a third value for the third attribute associated with the first device based on the second set of data packets;
    selecting a second subset of the set of classifiers, wherein the second subset of classifiers includes the third classifier that is associated with the third attribute;
    applying at least the third value for the third attribute to the third classifier to determine a third candidate device profile, of the plurality of candidate device profiles, for the first device;
    based at least on the third candidate device profile, determining the third candidate device profile as the current device profile for the first device.

3. The medium of claim 1, wherein the one or more expected values for the first attribute is determined based on a centroid of a cluster determined for the current device profile using machine learning.

4. The medium of claim 1, wherein the corrective action comprises one or more of:
    transmitting an alert;
    disconnecting the first device from the network;
    prohibiting the first device from connecting to the network;
    quarantining the first device.

5. The medium of claim 1, wherein the operations further comprise:
    obtaining a second set of one or more data packets associated with a second communication session conducted by the first device;
    determining the particular value for the first attribute associated with the first device based on the second set of data packets.

6. The medium of claim 1, wherein the first attribute comprises at least one of:
    an attribute associated with a flow of the communication session;
    an attribute associated with a Domain Name System (DNS) protocol used by the communication session;
    an attribute associated with a Dynamic Host Configuration Protocol (DHCP) used by the communication session;
    an attribute associated with a Digital Imaging and Communications in Medicine (DICOM) protocol used by the communication session;
    an attribute associated with a Point of Care Testing (POCT) protocol used by the communication session;

an attribute associated with a Common Industrial Protocol (CIP) used by the communication session;
an attribute associated with a Session Initiation Protocol (SIP) used by the communication session;
an attribute associated with a Real Time Streaming Protocol (RTSP) used by the communication session; and
an attribute associated with a Building Automation and Control network (BACnet) protocol used by the communication session.

7. The medium of claim 1, wherein the first set of one or more data packets are obtained using a set of sensors associated with at least one of: a distribution layer of a network hierarchy, and a core layer of the network hierarchy.

8. The medium of claim 1, wherein the operations further comprise:
extracting a first device identifier from the first set of data packets;
obtaining a second set of one or more data packets associated with a second communication session conducted by the first device;
determining a third value for a fourth attribute based on the second set of data packets;
extracting a second device identifier from the second set of data packets;
responsive to determining that the first device identifier and the second device identifier correspond to the first device:
determining the first value for the first attribute and the third value for the fourth attribute are associated with the first device.

9. The medium of claim 8, wherein the operations further comprise:
applying at least the third value for the fourth attribute to a fourth classifier to determine a third candidate device profile, of the plurality of candidate device profiles, for the first device;
based at least on the first candidate device profile, the second candidate device profile, and the third candidate device profile, determining the first candidate device profile as the current device profile for the first device.

10. The medium of claim 1, wherein the particular value for the first attribute is the first value for the first attribute.

11. The medium of claim 1, wherein the operations further comprise:
determining whether another particular value for the first attribute matches the one or more expected values for the first attribute;
responsive to determining that the another particular value for the first attribute matches the one or more expected values for the first attribute: refraining from performing the corrective action.

12. A system, comprising:
at least one device including a hardware processor; and
the system being configured to perform operations comprising:
obtaining a first set of one or more data packets associated with a communication session conducted by a first device in a network;
determining a first value for a first attribute associated with the first device based on the first set of data packets;
determining a second value for a second attribute associated with the first device based on the first set of data packets;
determining that any value for a third attribute associated with the first device has not been determined based on the first set of data packets;
selecting a subset of a set of classifiers, wherein the subset of classifiers:
includes a first classifier that is associated with the first attribute;
includes a second classifier that is associated with the second attribute;
does not include a third classifier that is associated with the third attribute;
applying at least the first value for the first attribute to the first classifier to determine a first candidate device profile, of a plurality of candidate device profiles, for the first device;
applying at least the second value for the second attribute to the second classifier to determine a second candidate device profile, of the plurality of candidate device profiles, for the first device;
refraining from using the third classifier to determine any candidate device profile for the first device;
based at least on the first candidate device profile and the second candidate device profile, determining the first candidate device profile as a current device profile for the first device;
wherein determining the first candidate device profile as the current device profile for the first device comprises:
determining a first weight associated with the first classifier;
determining a second weight associated with the second classifier;
determining a first profile score for the first candidate device profile based at least on the first weight;
determining a second profile score for the second candidate device profile based at least on the second weight;
determining that the first profile score is greater than the second profile score;
determining one or more expected values for the first attribute based on the current device profile;
determining whether a particular value for the first attribute matches the one or more expected values for the first attribute;
responsive to determining that the particular value for the first attribute does not match the one or more expected values for the first attribute: performing a corrective action.

13. The system of claim 12, wherein the operations further comprise:
subsequent to determining the current device profile for the first device:
obtaining a second set of one or more data packets associated with a second communication session conducted by the first device;
determining a third value for the third attribute associated with the first device based on the second set of data packets;
selecting a second subset of the set of classifiers, wherein the second subset of classifiers includes the third classifier that is associated with the third attribute;
applying at least the third value for the third attribute to the third classifier to determine a third candidate device profile, of the plurality of candidate device profiles, for the first device;
based at least on the third candidate device profile, determining the third candidate device profile as the current device profile for the first device.

14. The system of claim 12, wherein the one or more expected values for the first attribute is determined based on a centroid of a cluster determined for the current device profile using machine learning.

15. The system of claim 12, wherein the corrective action comprises one or more of:
   transmitting an alert;
   disconnecting the first device from the network;
   prohibiting the first device from connecting to the network;
   quarantining the first device.

16. The system of claim 12, wherein the operations further comprise:
   obtaining a second set of one or more data packets associated with a second communication session conducted by the first device;
   determining the particular value for the first attribute associated with the first device based on the second set of data packets.

17. The system of claim 12, wherein the particular value for the first attribute is the first value for the first attribute.

18. The system of claim 12, wherein the operations further comprise:
   determining whether another particular value for the first attribute matches the one or more expected values for the first attribute;
   responsive to determining that the another particular value for the first attribute matches the one or more expected values for the first attribute: refraining from performing the corrective action.

19. A method, comprising:
   obtaining a first set of one or more data packets associated with a communication session conducted by a first device in a network;
   determining a first value for a first attribute associated with the first device based on the first set of data packets;
   determining a second value for a second attribute associated with the first device based on the first set of data packets;
   determining that any value for a third attribute associated with the first device has not been determined based on the first set of data packets;
   selecting a subset of a set of classifiers, wherein the subset of classifiers:
      includes a first classifier that is associated with the first attribute;
      includes a second classifier that is associated with the second attribute;
      does not include a third classifier that is associated with the third attribute;
   applying at least the first value for the first attribute to the first classifier to determine a first candidate device profile, of a plurality of candidate device profiles, for the first device;
   applying at least the second value for the second attribute to the second classifier to determine a second candidate device profile, of the plurality of candidate device profiles, for the first device;
   refraining from using the third classifier to determine any candidate device profile for the first device;
   based at least on the first candidate device profile and the second candidate device profile, determining the first candidate device profile as a current device profile for the first device;
   wherein determining the first candidate device profile as the current device profile for the first device comprises:
      determining a first weight associated with the first classifier;
      determining a second weight associated with the second classifier;
      determining a first profile score for the first candidate device profile based at least on the first weight;
      determining a second profile score for the second candidate device profile based at least on the second weight;
      determining that the first profile score is greater than the second profile score;
   determining one or more expected values for the first attribute based on the current device profile;
   determining whether a particular value for the first attribute matches the one or more expected values for the first attribute;
   responsive to determining that the particular value for the first attribute does not match the one or more expected values for the first attribute: performing a corrective action;
   wherein the method is performed by at least one device including a hardware processor.

20. The method of claim 19, further comprising:
   subsequent to determining the current device profile for the first device:
   obtaining a second set of one or more data packets associated with a second communication session conducted by the first device;
   determining a third value for the third attribute associated with the first device based on the second set of data packets;
   selecting a second subset of the set of classifiers, wherein the second subset of classifiers includes the third classifier that is associated with the third attribute;
   applying at least the third value for the third attribute to the third classifier to determine a third candidate device profile, of the plurality of candidate device profiles, for the first device;
   based at least on the third candidate device profile, determining the third candidate device profile as the current device profile for the first device.

21. The method of claim 19, wherein the one or more expected values for the first attribute is determined based on a centroid of a cluster determined for the current device profile using machine learning.

22. The method of claim 19, wherein the corrective action comprises one or more of:
   transmitting an alert;
   disconnecting the first device from the network;
   prohibiting the first device from connecting to the network;
   quarantining the first device.

23. The method of claim 19, further comprising:
   obtaining a second set of one or more data packets associated with a second communication session conducted by the first device;
   determining the particular value for the first attribute associated with the first device based on the second set of data packets.

* * * * *